US007806828B2

(12) United States Patent
Stringer

(10) Patent No.: US 7,806,828 B2
(45) Date of Patent: Oct. 5, 2010

(54) MULTIPLANAR ULTRASONIC VASCULAR SENSOR ASSEMBLY AND APPARATUS FOR MOVABLY AFFIXING A SENSOR ASSEMBLY TO A BODY

(75) Inventor: Bradley J. Stringer, Farmington, UT (US)

(73) Assignee: Inceptio Medical Technologies, LC, Farmington, UT (US)

( * ) Notice: Subject to any disclaimer, the term of this patent is extended or adjusted under 35 U.S.C. 154(b) by 529 days.

(21) Appl. No.: 11/364,811

(22) Filed: Feb. 28, 2006

(65) Prior Publication Data

US 2007/0016030 A1   Jan. 18, 2007

Related U.S. Application Data

(60) Continuation-in-part of application No. 10/911,860, filed on Aug. 3, 2004, which is a continuation of application No. 10/872,699, filed on Jun. 21, 2004, now Pat. No. 7,214,191, which is a division of application No. 10/072,662, filed on Feb. 5, 2002, now Pat. No. 6,755,789.

(51) Int. Cl.
*A61B 8/00* (2006.01)
(52) U.S. Cl. .................. 600/461; 600/459; 600/437
(58) Field of Classification Search .......... 600/437–472
See application file for complete search history.

(56) References Cited

U.S. PATENT DOCUMENTS

| | | | |
|---|---|---|---|
| 3,556,079 A | | 1/1971 | Omizo |
| 3,758,202 A | * | 9/1973 | Chunga, Sr. .................. 351/41 |
| 3,777,740 A | | 12/1973 | Hokanson |
| 3,888,238 A | * | 6/1975 | Meindl et al. ................ 600/455 |
| 4,067,342 A | | 1/1978 | Burton |
| 4,092,867 A | * | 6/1978 | Matzuk ........................ 73/609 |

(Continued)

FOREIGN PATENT DOCUMENTS

EP   0 341 718 A1   11/1989

(Continued)

OTHER PUBLICATIONS

Partial International Search Report, dated Jul. 22, 2003.

(Continued)

*Primary Examiner*—Long V Le
*Assistant Examiner*—Nigel Fontenot
(74) *Attorney, Agent, or Firm*—TraskBritt

(57) ABSTRACT

An apparatus is provided for cannulation of blood vessels. The apparatus comprises a sensor assembly including two linear transducer arrays oriented perpendicular to each other to form a "T" shape to provide ultrasound images of at least one blood vessel in a portion of a patient's body in two perpendicular planes. The sensor assembly includes a housing having a graphically marked surface to facilitate orientation of the sensor assembly on the patient and guidance of a needle toward a desired target vessel during the cannulation procedure. The housing is configured to engage a frame element having a pair of wings extending laterally therefrom, the wings each bearing a magnet to cooperate with a reference location element secured to a patient's skin and bearing magnetically responsive shims thereon to place, align and secure the sensor assembly to the patient's skin at a desired location.

11 Claims, 13 Drawing Sheets

U.S. PATENT DOCUMENTS

| | | | |
|---|---|---|---|
| 4,143,650 A | | 3/1979 | Hatke |
| 4,259,965 A | | 4/1981 | Fukuda et al. |
| 4,373,533 A | * | 2/1983 | Iinuma ..................... 600/441 |
| 4,402,324 A | * | 9/1983 | Lindgren et al. ............ 600/461 |
| 4,408,692 A | | 10/1983 | Sigel et al. |
| 4,475,553 A | | 10/1984 | Yamaguchi et al. |
| 4,593,699 A | | 6/1986 | Poncy et al. |
| 4,622,978 A | | 11/1986 | Matsuo et al. |
| 4,646,722 A | | 3/1987 | Silverstein et al. |
| 4,794,933 A | | 1/1989 | Yamazaki |
| 4,869,258 A | | 9/1989 | Hetz |
| 4,887,606 A | | 12/1989 | Yock et al. |
| 4,947,853 A | * | 8/1990 | Hon ........................ 600/459 |
| 5,071,433 A | | 12/1991 | Naestoft et al. |
| 5,076,279 A | * | 12/1991 | Arenson et al. ............ 600/461 |
| 5,080,103 A | | 1/1992 | Olivier |
| 5,136,825 A | | 8/1992 | White, Jr. |
| 5,167,629 A | | 12/1992 | Vertenstein et al. |
| 5,168,863 A | | 12/1992 | Kurtzer |
| 5,220,923 A | | 6/1993 | Hagiwara et al. |
| 5,259,383 A | | 11/1993 | Holstein et al. |
| 5,259,386 A | | 11/1993 | Sharkawy |
| 5,261,407 A | | 11/1993 | Nishigaki et al. |
| 5,272,625 A | | 12/1993 | Nishihara et al. |
| 5,311,871 A | | 5/1994 | Yock |
| 5,329,699 A | | 7/1994 | McCoy |
| 5,351,698 A | | 10/1994 | Wheeler et al. |
| 5,363,852 A | | 11/1994 | Sharkawy |
| 5,394,877 A | | 3/1995 | Orr et al. |
| 5,427,108 A | | 6/1995 | Bollinger |
| 5,469,853 A | | 11/1995 | Law et al. |
| 5,490,522 A | | 2/1996 | Dardel |
| 5,520,657 A | | 5/1996 | Sellers et al. |
| 5,546,807 A | | 8/1996 | Oxaal et al. |
| 5,664,573 A | | 9/1997 | Shmulewitz |
| 5,722,412 A | | 3/1998 | Pflugrath et al. |
| 5,742,389 A | | 4/1998 | Zavislan et al. |
| 5,762,616 A | * | 6/1998 | Talish ........................ 601/2 |
| 5,779,625 A | | 7/1998 | Suzuki et al. |
| 5,855,558 A | | 1/1999 | Nakao et al. |
| 5,891,039 A | | 4/1999 | Bonnefous et al. |
| 5,910,113 A | | 6/1999 | Pruter |
| 5,957,850 A | | 9/1999 | Marian, Jr. et al. |
| 6,014,473 A | | 1/2000 | Hossack et al. |
| 6,045,508 A | | 4/2000 | Hossack et al. |
| 6,048,323 A | * | 4/2000 | Hon ........................ 600/588 |
| 6,117,152 A | | 9/2000 | Huitema |
| 6,122,538 A | | 9/2000 | Sliwa, Jr. et al. |
| 6,128,002 A | | 10/2000 | Leiper |
| 6,132,379 A | | 10/2000 | Patacsil et al. |
| 6,137,487 A | | 10/2000 | Mantha |
| 6,203,499 B1 | | 3/2001 | Imling et al. |
| 6,224,543 B1 | | 5/2001 | Gammons et al. |
| 6,261,234 B1 | | 7/2001 | Lin |
| 6,293,907 B1 | | 9/2001 | Axon et al. |
| 6,293,914 B1 | | 9/2001 | Sumanaweera et al. |
| 6,370,413 B1 | | 4/2002 | Alvarez et al. |
| 6,377,162 B1 | | 4/2002 | Delestienne et al. |
| 6,422,474 B1 | | 7/2002 | Gossweiler et al. |
| 6,423,002 B1 | | 7/2002 | Hossack |
| 6,464,507 B1 | | 10/2002 | Bailey |
| 6,480,732 B1 | | 11/2002 | Tanaka et al. |
| 6,540,679 B2 | | 4/2003 | Slayton et al. |
| 6,824,511 B1 | | 11/2004 | Bell et al. |
| 7,410,469 B1 | * | 8/2008 | Talish et al. .................... 601/2 |
| 2002/0058872 A1 | | 5/2002 | Steininger et al. |
| 2002/0087080 A1 | * | 7/2002 | Slayton et al. ............. 600/459 |
| 2002/0120332 A1 | | 8/2002 | Law et al. |
| 2004/0186356 A1 | | 9/2004 | O'Malley et al. |

FOREIGN PATENT DOCUMENTS

| | | |
|---|---|---|
| EP | 0 376 396 A2 | 7/1990 |
| EP | 0 467 291 A1 | 1/1992 |
| EP | 0 477 581 A1 | 4/1992 |
| WO | 99/56829 A1 | 11/1999 |

OTHER PUBLICATIONS

PCT International Search Report, dated Nov. 21, 2003.

AHRQ (Agency for Health Care Research and Quality) Study, Making Health Care Safer, A Critical Analysis of Patient Safety Practices, Evidence Report/Technology Assessment, No. 43, (no date), 11 pages.

Albin, M.S. "Air Embolism." Embolism II, 11, 1, Mar. 1993, 1-24.

Alderson, P.J., Burrows, F.A. "The Use of Ultrasound to Facilitate Central Venous Cannulation in Young Children." Anesthesiology, 77, 3A, Sep. 1992, A1196.

Andrews, R.T., Bova, D.A., Venbrux, A.C. "How much Guidewire is too much? Direct Measurement of the Distance from Subclavian and Internal Jugular Vein Access Sites to the Superior Vena Cava-Atrial Junction During Central Venous Catheter Placement." Critical Care Medicine, 2000, 28, 1, 138-142.

Andrews, R.T., Osterman, F.A. "Technical Note: Antegrade Access to the Superficial Femoral Artery Using a Dedicated Vascular Access Ultrasound Device." Applied Radiology, Aug. 1998, 33-36.

Aoki, H., Mizobe, T., Nozuchi, S., et al. "Vertebral Artery Pseudoaneurysm: A Rare Complication of Internal Jugular Vein Catheterization." Anesth Analg, 1992, 75, 296-298.

Applebaum, R.M., Adelman, M.A., Kanschuger, M.S., Jacobowitz, G., Kronzon, I. "Transesophageal Echocardiographic Identification of a Retrograde Dissection of the Ascending Aorta Caused by Inadvertent Cannulation of the Common Carotid Artery." Journal of the American Society of Echocardiography, 10, 7, Sep. 1997, 749-751.

Arditis, J., Giala, M., Anagnostidou, A.. "Accidental Puncture of the Right Lymphatic Duct During Pulmonary Artery Catheterization. A Case Report." Acta Anaesthesiologica Scandinavica, 1988, 32, 67-68.

Armstrong, P.J., Sutherland, R., Scott, D.H.T. "The Effect of Position and Different Maneuvers on Internal Jugular Vein Diameter Size." Acta Anaesthesiologica Scandinavica, 1994, 38, 229-231.

"Aspen Ultrasound System, Imagegate Release," www.acuson.com/aspen/home_aspen_rad.html, © 2002, (4 pages), Acuson, A Siemens Company.

Armstrong, P.J., Cullen, M., Scott, D.H.T., "The 'SiteRite'Ultrasound Machine—An Aid to Internal Jugular Vein Cannulation," Anaesthesia, 1993, vol. 48, pp. 319-323.

Arnold, S., Feathers, R.S., Gibbs, E. "Bilateral Pneumothraces and Subcutaneous Emphysema: A Complication of Internal Jugular Venepuncture," British Medical Journal, 1973, 1, 211-212.

Asheim, P. Aadahl, P. Fasting, S. "[Ultrasound Guidance for Placement of Central Venous Catheters]." Tidsskr Nor Loegeforen, 24, 1999, 119, 3605-3606.

Bailey, A.R. "A Close Shave: Air Embolism Following Laceration of Central Venous Catheter." Anaesthesia, 51, Mar. 1996, 294.

"Bard, Site-Rite Ultrasound System," wwwdymax-usa.com, © 2001, (8 pages), Dymax Corporation.

Bazaral, M., Harlan, S. "Ultrasound Anatomy of the Internal Jugular Vein Relevant to Percutaneous Cannulation." Critical Care Medicine, Apr. 1981, 9, 4, 307-310.

Blank, R., Rupprecht, H.J., Schorrlepp, M., Kopp, H., Rahmani, R. "[Clinical Importance of Ultrasonic Sound Guided Puncture of Femoral Vessels with Smart Needle in Cardiac Catheterization]." Zeitschrift fuer Kardiologie, 86, 8, 1997, 608-614.

Brass, P., Volk, O., Leben, J., Schregel, W. "[Central Venous Cannulation—Always with Ultrasound Support?]." Anaesthesiol Intensivmed Notfallmed Schmerzther, 2001, 36, 619-627.

Burns, S., Herbison, G.J. "Signal Accessory Nerve Injury as a Complication of Internal Jugular Vein Cannulation." Annals of Internal Medicine, Oct. 15, 1996, 125, 8, 700.

Caridi, J.G., Hawkins, I.F., et al. "Sonographic Guidance when Using the Right Internal Jugular Vein for Central Vein Access." AJR, 171, Nov. 1998, 1259-1263.

Colley, D.P. "Vertebral Arteriovenous Fistula: An Unusual Complication of Swan-Ganz Catheter Insertion." AJNR, 6, Jan./Feb. 1985, 103-104.

Conz, P.A., Dissegna, D., Rodighiero, M.P., LaGreca, G. "Cannulation of the Internal Jugular Vein: Comparison of the Classic Seldinger Technique and an Ultrasound Guided Method." Journal of Nephrology, 10, 6, 1997, 311-313.

Damen, J., Bolton, D. "A Prospective Analysis of 1400 Pulmonary Artery Catheterizations in Patients Undergoing Cardiac Surgery." Acta Anaesthesiologica Scandinavica, 1986, 30, 386-392.

Davies, M.J., Cronin, K.D., Comaingue, C.M. "Pulmonary Artery Catheterisation: An Assessment of Risks and Benefits on 220 Surgical Patients." Anaesthesia and Intensive Care, X, 1, Feb. 1982, 9-14.

Denys, B.G., Uretsky, B.F., Reddy, P.S. "Ultrasound-Assisted Cannulation of the Internal Jugular Vein. A Prospective Comparison to the External Landmark-Guided Technique." Circulation, 87, 5, May 1993, 1557-1562.

Depierraz, B., Essinger, A., Morin, D., Goy, J.J., Buchser, E. "Isolated Phrenic Nerve Injury After Apparently Atraumatic Puncture of the Internal Jugular Vein." Intensive Care Medicine, 1989, 15, 132-134.

Doblar, D.D., Hinkle, J.C., Fay, M.L., Condon, B.F. "Air Embolism Associated with Pulmonary Artery Catheter Introducer Kit." Anesthesiology, 56, 307, 1982.

Downie, A.C., Reidy, J.F., Adam, A.N. "Short Communication: Tunnelled Central Venous Catheter Insertion via the Internal Jugular Vein Using a Dedicated Portable Ultrasound Device." British Journal of Radiology, Feb. 1996, 69, 818, 178-181.

Eckhardt, W.F., Iaconetti, D.J., Kwon, J.S., et al. "Inadvertent Carotid Artery Cannulation During Pulmonry Artery Catheter Insertion." Journal of Cardiothoracic and Vascular Anesthesia, 10, 2 (February), 1996, 283-290.

Ellerbrock, U. "[Neurological Complications in Connection with the Placing of a Catheter Into the Internal Jugular Vein]." Anaesthesist, 1984, 33, 121-122.

Farrell, J., Gellens, M. "Ultrasound Guided Cannulation versus the Landmark-Guided Technique for Acute Haemodialysis Access." Nephrology Dialysis Transplantation, 1997, 12, 1234-1237.

Ferrall, H. "US-Guided Puncture of the Internal Jugular Vein: An Unexpected Anatomic Relationship." JVIR, 9, 5, Sep.-Oct. 1998, 854-855.

Fleischer, F., Fleischer, E., Krier, C. "[The Internal Jugular Vein Catheter—Success and Complication and its Relation to Experience]." Anaesthesiol Intensivmed Notfallmed Schmerzther, 22, 1987, 94-98.

Fry, W.R., Clagett, G.C., O''Rourke, P.T. "Ultrasound-Guided Central Venous Access." Arch. Surg., 134, Jul. 1999, 738-741.

Gilbert, T.B., Seneff, M.G., Becker, R.B. "Facilitation of Internal Jugular Venous Cannulation Using an Audio-Guided Doppler Ultrasound Vascular Access Device: Results From a Prospective, Dual-Center, Randomized, Crossover Clinical Study." Critical Care Medicine, 23, 1, Jan. 1995, 60-65.

Gobeil, F., Couture, P., Girard, D., Plante, R. "Carotid Artery-Internal Jugular Fistula: Another Complication Following Pulmonary Artery Catheterization Via the Internal Jugular Venous Route." Anesthesiology, 80, 1, Jan. 1994, 230-232.

Golden, L.R. "Incidence and Management of Large-Bore Introducer Sheath Puncture of the Carotid Artery." Journal of Cardiothoracic and Vascular Anethesia, 9, 4 (August), 1995, 425-428.

Gordon, A.C., Saliken, J.C., et al. "US-Guided Puncture of the Internal Jugular Vein: Complications and Anatomic Considerations." JVIR, 1998, 9, 2 (March/April), 333-338.

Gratz, I., Afshar, M., et al. "Doppler-Guided Cannulation of the Internal Jugular Vein: A Prospective, Randomized Trial." Journal of Clinical Monitoring, 10, 3, May 1994, 185-188.

Guezeldemir, M.E., Uestuensoez, B. "Ultrasonographic Guidance in Placing a Catheter for Continuous Auxiliary Brachial Plexus Block." Anesth Analg, 1995, 81, 882-883.

Haro, M., Izquierdo, M., et al. "[Diaphragm Paralysis as a Complication of Puncture of the Internal Jugular Vein]." Archivos de Bronconeumologia, 32, 2, 1996, 105-107.

Hastings, G.S., et al., "Compulsory Use of Site-Rite Sonographic Guidance for Low Internal Jugular Vein Access Eliminates Major Puncture-Related Complications," No. 68, p. S90 (date unknown).

Hatfield, A. and Bodenham, A. "Portable Ultrasound for Difficult Central Venous Access." British Journal of Anaesthesia, 82, 6, 822-826 (1999).

Hayashi, Y. "A Lethal Complication of Internal Jugular Vein Catheterization." Anesth Analg, 1993, 76, 910.

Hayashi, Y., Uchida, O., Takaki, O., et al. "Internal Jugular Vein Catheterization in Infants Undergoing Cardiovascular Surgery: An Analysis of the Factors Influencing Successful Catheterization." Anesth Analg, 1992, 74, 688-693.

Heatly, T., et al., "Comparison of the Conventional Landmark Technique and an Ultrasound-Guided Approach for the Placement of Central Venous Indwelling Catheters," p. A333 (date unknown).

Ho, A.M.-H., Chung, D.C., Tay, B.A., Yu, L.M., Yeo, P. "Diluted Venous Blood Appears Arterial: Implications for Central Venous Cannulation." Anesth Analg, 2000, 91, 1356-1357.

Hrics, P., Wilber, S., Blanda, M.P., Gallo, U. "Ultrasound-Assisted Internal Jugular Vein Catheterization in the ED." American Journal of Emergency Medicine, 16, 4, Jul. 1998, 401-403.

Hudson, P.A., Rose, J.S. "Real-time Ultrasound Guided Internal Jugular Vein Catheterization in the Emergency Department." American Journal of Emergency Medicine, 15, 1, Jan. 1997, 79-82.

Hullander, M., Spillane, W., Leivers, D., Balsara, Z. "The Use of Doppler Ultrasound to Assist with Sciatic Nerve Blocks." Regional Anesthesia, 1991, 16, 282-284.

Irita, K., et al., "Tension Hemothorax Caused by Inadvertent Insertion of an Introducer/Dilator Into the Vertebral Artery," Letters to the Editor, pp. 241-242 (date unknown).

Iserson, K.V., Copeland, J. "Pulmonary and Aortic Punctures—Complications of an Attempt at Internal Jugular Venipuncture." Journal of Emergency Medicine, 1984, 1, 227-231.

Jain, U., Shah, K.B., Belusko, R.J., et al. "Subclavian Artery Laceration and Acute Hemothorax on Attempted Internal Jugular Vein Cannulation." Journal of Cardiothoracic and Vascular Anesthesia, 5, 6 (December), 1991, 608-610.

Jarosz, J.M., McKeown, B., Reidy, J.F. "Short-term Femoral Nerve Complications Following Percutaneous Transfemoral Procedures." JVIR, May-Jun. 1995, 6, 351-353.

Kayashima, K., et al., "A Reliable Method for Internal Jugular Vein Catheterization for Neonates and Infants Using a Small-Caliber Doppler Probe," Dept. of Anesthesia, Kyushu-Koseinenkin Hospital, Kitakyushu, 806, 1996, pp. 1424-1429.

Kihara, S, et al., "Central Venous Access Via the Distal Femoral Vein Using Ultrasound-Guidance," Dept. of Anesthesiology and Institute of Clinical Medicine, Univ. of Tsukuba, Tsukuba, 305-8575, Dept. of Anesthesiology and Intensive Care, Hamamatsu Univ. School of Medicine, Hamamatsu, 431-3124, 1998, pp. 1253-1257.

Knoblanche, G.E. "Respiratory Obstruction Due to Haematoma Following Internal Jugular Vein Cannulation." Anaesthesia and Intensive Care, VII, 3, Aug. 1979, 286.

Kocis, K.C., Vermilion, R.P., Callow, L.B., et al. "Complications of Femoral Artery Cannulation for Perioperative Monitoring in Children." The Journal of Thoracic and Cardiovascular Surgery, 112, 5, 1399-1400.

Konichezky, S., Saguib, S., Soroker, D. "Tracheal Puncture. A Complication of Percutaneous Internal Jugular Vein Cannulation." Anaesthesia, 1983, 38, 572-574.

Kua, J.S.W., Tan, I.K.S. "Airway Obstruction Following Internal Jugular Vein Cannulation." Anaesthesia, 1997, 52, 776-780.

Kuebler, A., Golebiowska, B., Plawiak, T. "[Ultrasound Guided Cannulation of Internal Jugular Vein]." Przeglad Lekarski, 1997, 54, 11, 802-805.

Kwon, T.H., Kim, Y.L., Cho, D.K. "Ultrasound-Guided Cannulation of the Femoral Vein for Acute Haemodialysis Access." Nephrology Dialysis Transplantation, 1997, 12, 1009-1012.

La Grange, P. du P., Foster, P.A., Pretorius, L.K. "Application of the Doppler Ultrsound Bloodflow Detector in Supraclavicular Brachial Plexus Block." British Journal of Anaesthesia, 1978, 50, 965-967.

Lampmann, L.E.H., Schuur, K.H. "Utilization of Ultrasound Guidance in Difficult Femoral Artery Puncture." European Journal of Radiology, 18, 1994, 20-21.

Lane, P., Waldron, R.J. "Real-Time Ultrasound-Guided Central Venous Access via the Subclavian Approach." Anaesthesia and Intensive Care, 23, 6, Dec. 1995, 728-730.

Lang, S.A. "Ultrasound and the Femoral Three-in-One Nerve Block: Weak Methodology and Inappropiate Conclusions." Anesth Analg, 1998, 86, 1147-1148.

Lennon, P. "Dural Puncture as a Complication of Internal Jugular Vein Cannulation." Anesthesiology, 85, 4, Oct. 1996, 944.

Liberman, L., Hordof, A.J., Hsu, D.T., Pass, R.H. "Ultrasound-Assisted Cannulation of the Right Internal Jugular Vein During Electrophysiologic Studies in Children." Journal of Interventional Cardiac Electrophysiology, 2001, 5, 177-179.

Lichtenstein, et al., "The Internal Jugular Veins are Asymmetric. Usefulness of Ultrasound Before Catheterization." Intensive Care Medicine, 2001, 27, 301-305.

Lips, U., Conrad, I., Zevounou, F. Schappler-Scheele, B. "[Report on Two Cases of Irreversible Horner''s Syndrome After Puncture of the Internal Jugular Vein]." Anaesthesiol Intensivmed Notfallmed Schmerzther, 1982, 17, 301-302.

Lobato, E.B., Sulek, C.A., Moody, R.L., Morey, T.E. "Cross-Sectional Area of the Right and Left Internal Jugular Veins." Journal of Cardiothoracic and Vascular Anesthesia, 13, 2 (April), 1999, 136-138.

MacIntyre, P.A., Samra, G., Hatch, D.J. "Preliminary Experience with the Doppler Ultrasound Guided Vascular Access Needle in Paediatric Patients." Paediatric Anaesthesia, 2000, 10, 361-365.

Majeski, J.A. "Vertebral Arteriovenous Fistula as a Result of Swan-Ganz Catheter Insertion: Surgical Correction in a Symptomatic Patient." Int Surg, 1999, 84, 74-77.

Mallory, D.L., McGee, W.T., et al. "Ultrasound Guidance Improves the Success Rate of Internal Jugular Vein Cannulation. A Prospective, Randomized Trial." Chest, 98, 1, Jul. 1990, 157-160.

Marhofer, P., Schroegendorfer, K., et al. "Ultrasonographic Guidance Improves Sensory Block and Onset Time of Three-in-One Blocks." Anesth Analg, 1997, 85, 854-857.

Mbamalu, D., et al., "Methods of Obtaining Peripheral Venous Access in Difficult Situations," Classic Techniques in Medicine, Mar. 1999, pp. 159-162.

McGee, D.C., et al., "Preventing Complications of Central Venous Catheterization," New England Jour. Of Medicine (on-line), vol. 348, No. 12, pp. 1123-1133, Mar. 20, 2003.

McNulty, S.E., "Ultrasound-Assisted Central Venous Cannulation: Resident Teaching Tool or Practice Standard?," American Jour. Of Anesthesiology, Sep. 2000, pp. 388-389.

Mennim, P., Coyle, C.F., Taylor, J.D. "Venous Air Embolism Associated with Removal of Central Venous Catheter." BMJ, 1992, 305, 171-172.

Miller, J.A., Singireddy, S., Maldjian, P., Baker, S.R. "A Reevaluation of the Radiographically Detectable Complications of Percutaneous Venous Access Lines Inserted by Four Suncutaneous Approaches." The American Surgeon, Feb. 1999, 65, 125-130.

Mitchell, S.E., Clark, R.A. "Complications of Central Venous Catheterization." AJR, 133, Sep. 1979, 467-476.

Moellmann, M., von Hornstein, W.F., et al. "Percutaneous Venous Cannulation and Central Venous Line Placement by Means of Ultrasonography and Ultrasonic Doppler." Acta Anaesthesiologica Belgica, 1990, 41, 345-351.

Muhm, M., Waltl, B., Sundur-Plassmann, G., Apsner, R. "Is Ultrasound Guided Cannulation of the Internal Jugular Vein Really Superior to Landmark Techniques?" Nephrology Dialysis Transplantation, 1998, 13, 522-524.

NICE (National Institute for Clinical Excellence) Study, Final Appraisal Determination: Ultrasound location devices for placing central venous catheters, Jul. 2002, 17 pages.

Paschall, R.M., Mandel, S. "Brachial Plexus Injury from Percutaneous Cannulation of the Internal Jugular Vein." Annals of Emergency Medicine, 12, 1, Jan. 1983, 58-60.

Patel, C., Laboy, V., Venus, B., Mathru, M., Wier, D. "Acute Complications of Pulmonary Artery Catheter Insertion in Critically Ill Patients." Critical Care Medicine, 14, 3, 195-197.

Piechowiak, H., Buechels, H., Ingrisch, H., Hess, H. "Arteriovenous Fistula of the Vertebral Artery: A Rare Complication of Percutaneous Central Vein Puncture. A Case Report." Anaesthesist, 1984, 33, 327-329.

Pierce, E.T., Hunter, J., Bode, R.H., Lewis, K.P., Satwicz, P. "Ultrasound Guidance Facilitates Cannulation of the Femoral Artery." Anesthesiology, 81, 3A, Sep. 1994, A542.

Randolph, A.G., Cook, D.J., Gonzales, C.A., Pribble, C.G. "Ultrasound Guidance for Placement of Central Venous Catheters: A Meta-Analysis of the Literature." Critical Care Medicine, 1996, 24, 12, 2053-2058.

Reed, J., Leighton, S. "Ultrasound Facilitation of Brachial Plexus Block." Anaesthesia and Intensive Care, 22, 4, Aug. 1994, 499.

Riopelle, J., "Stroke from Mistaken Carotid Puncture Promotes Interest in Neck Vein Finders," APSF Newsletter, Fall 2000, p. 41.

Riopelle, J.M., Busch, E.H., Wood, D.G., et al. "Ultrasound-Guided Internal Jugular Venous Cannulation: An Introduction for Non-Radiologists to a Technique That is Here to Stay." J La State Med Soc, 153, Feb. 2001, 142-152.

Sakai, M., et al., "A Case of Right Phrenic Nerve Paralysis as a Complication of Internal Jugular Vein Cannulation by Anterior Approach," Dept. of Anesthesiology, Osaka Medical College, Osaka 569, 1993, pp. 1355-1358.

Sato, S., Ueno, E., Toyooka, H. "Central Venous Access via the Distal Femoral Vein Using Ultrasound Guidance." Anesthesiology, 88, 3, Mar. 1998, 838-839.

Scherhag, A., Klein, A., Jantzen, J.P. "[Cannulation of the Internal Jugular Vein Aided by Two Ultrasonic Methods]." Anaesthesist, 1989, 38, 633-638.

Scott, D.H.T. ""In the Country of the Blind, the One-Eyed Man is King", Erasmus (1466-1536)."British Journal of Anaesthesia, (1999) 82, 6, 820-821.

Seldinger, S.I. "Catheter Replacement of the Needle in Percutaneous Arteriography." Acta Radiologica, 39, 368-376.

Sha, K., Simokawa, M., Kawaguchi, M., et al. "Use of Transesophageal Echocardiography Probe Imaging to Guide Internal Jugular Vein Cannulation." Anesth Analg, 1998, 87, 1032-1033.

Sheild, C.F., Richardson, J.D., Buckley, C.J., Hagood, Jr., C.O. "Pseudoaneurysm of the Brachiocephalic Arteries: A Complication of Percutaneous Internal Jugular Vein Catheterization." Surgery, Aug. 1975, 78, 2, 190-194.

Shulman, M.S., Kaplan, D.B., Lee, D.L. "An Anteromedial Internal Jugular Vein Successfully Cannulated Using the Assistance of Ultrasonography." Journal of Clinical Anesthesia, 12, Feb. 2000, 83-86.

Sing, R.F., Steffe, T.J., Branas, C.C. "Fatal Venous Air Embolism after Removal of a Central Venous Catheter." JAOA, 95, 3, Mar. 1995, 204-205.

Slama, M., Novara, A., Safavian, A., et al. "Improvement of Internal Jugular Vein Cannulation Using an Ultrasound-Guided Technique." Intensive Care Medicine, 1997, 23, 916-919.

Sloan, M.A., Mueller, J.D., Adelman, L.S., Caplan, L.R. "Fatal Brainstem Stroke Following Internal Jugular Vein Catheterization." Neurology, Jul. 1991, 41, 1092-1095.

Steinsapir, E.S., Coley, B.D., Fellmeth, B.D., Roberts, A.C., Hye, R.J. "Selective Management of Iatrogenic Femoral Artery Injuries." Journal of Surgical Research, 55, 1, Jul. 1993, 109-113.

Stern, W., Sauer, W., Dauber, W. "[Complications of Central Venous Catheterization From an Anatomical Point of View]." Acta Anat, 1990, 138, 137-143.

Sulek, C.A., et al., "Central Venous Cannulation Should be Performed Using Ultrasound Guidance," Drug & Innovations Review, vol. 1, No. 5, Oct. 2002, 4 pages.

Sylvestre, D.L., Sandson, T.A., Nachmanoff, D.B. "Transient Brachial Plexopathy as a Complication of Internal Jugular Vein Cannulation." Neurology, May 1991, 41, 760.

"The ACUSON Sequoia® 512 ultrasound platform ushers in a new era for diagnostic ultrasound," www.acuson.com/sequoia/sequoia_gi_home.html, © 2002, (3 pages), Acuson, A Siemens Company.

Timsit, J.F., Farkas, J.C., Boyer, J.M., et al. "Central Vein Catheter-Related Thrombosis in Intensive Care Patients. Incidence, Risks Factors, and Relationship With Catheter-Related Sepsis." Chest, 114, 1, Jul. 1998, 207-213.

"Toshiba, Medical Systems," http://medical.toshiba.com/clinical/cardiology/nemio153.html, © 2002, (2 pages), Toshiba.

Traber, K.B., Gilfor, J.M., Jobes, D.R. "Ultrasound-Assisted Cannulation of the Internal Jugular Vein: A Survey of Resident Use After Graduation." Anesthesiology, 81, 3A, Sep. 1994, A1250.

Troianos, C.A., Jobes, D.R., Ellison, N. "Ultrasound Guided Cannulation of the Internal Jugular Vein." Anesthesiology, 73, 3A, Sep. 1990, A451.

Trottier, S.J., Todi, S., Veremakis, C. "Validation of an Inexpensive B-Mode Ultrasound Device for Detection of Deep Vein Thrombosis." Chest, 110, 6, Dec. 1996, 1547-1550.

Turnage, W.S., Harper, J.V. "Venous Air Embolism Occurring After Removal of a Central Venous Catheter." Anesth Analg, 1991, 72, 559-560.

Tyden, H. "Cannulation of the Internal Jugular Vein—500 Cases." Acta Anaesthesiologica Scandinavica, 1982, 26, 485-488.

"Ultrasound Technologies," www.ultrasound.demon.co.uk/Company.html, © 2002, (3 pages), Ultrasound Technologies Ltd.

Verghese, S., McGill, W.A., Patel, R., et al. "Approaches to Internal Jugular Vein Cannulation in Infants: Seeing, Hearing vs. Feeling." Anesth Analg, 1995, 80, S525.

Verghese, S., McGill, W.A., Patel, R., et al. "Internal Jugular Vein Cannulation in Infants: Palpation vs. Imaging." Anesthesiology, 85, 3A, Sep. 1996, A1078.

Verghese, S.T., McGill, W.A., Patel, R.I., et al. "Ultrasound-Guided Internal Jugular Venous Cannulation in Infants. A Prospective Comparison with the Traditional Palpation Method." Anesthesiology, 91, 1, Jul. 1999, 71-77.

Verner, L., Stuetz, B. "[Cannulation of the Internal Jugular Vein by the Technique of Seldinger in a Patient with Severe Coagulopathy. Study About a Lethal Complication]." Anaesthesist, 1983, 185-186.

Vest, J.V., Pereira, M.B., Senior, R.M. "Phrenic Nerve Injury Associated with Venipuncture of the Internal Jugular Vein." Chest, 78, 5, Nov. 1980, 777-779.

Weimann, J., Frass, M., Traindl, O., Pidlich, J., Leithner, C. "[Acute Upper Airway Obstruction by Cervical Hematoma as a Complication of Internal Jugular Vein Catheterization]." AMA, 17/1990, 4, 77-79.

Whittet, H.B., Boscoe, M.J. "Isolated Palsy of the Hypoglossal Nerve After Central Venous Catheterisation." British Medical Journal, 288, Apr. 1984, 1042-1043.

Zaidi, N.A., Khan, M., Naqvi, H.I., Kamal, R.S. "Cerebral Infarct Following Central Venous Cannulation." Anaesthesia, 1998, 53, 186-191.

* cited by examiner

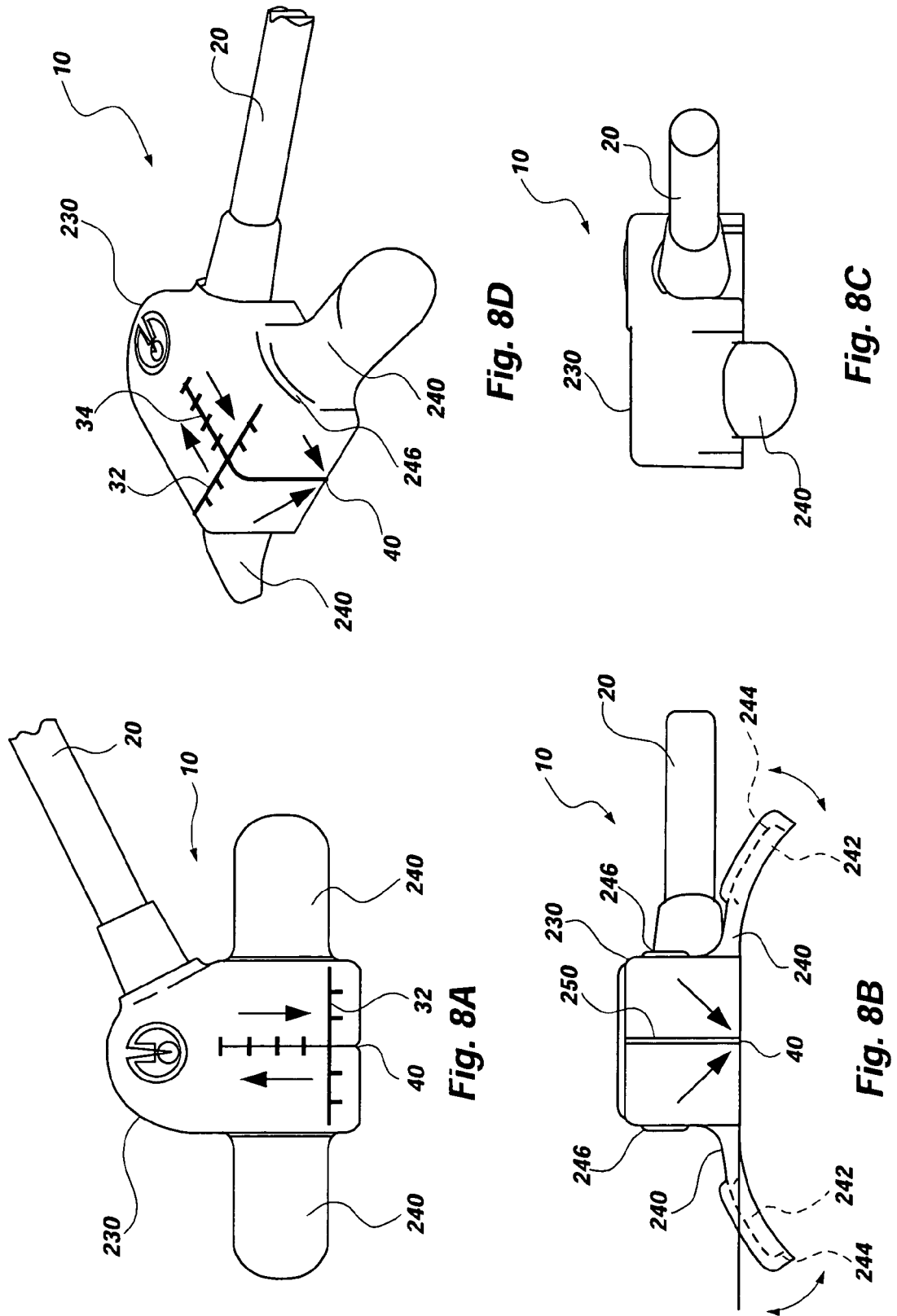

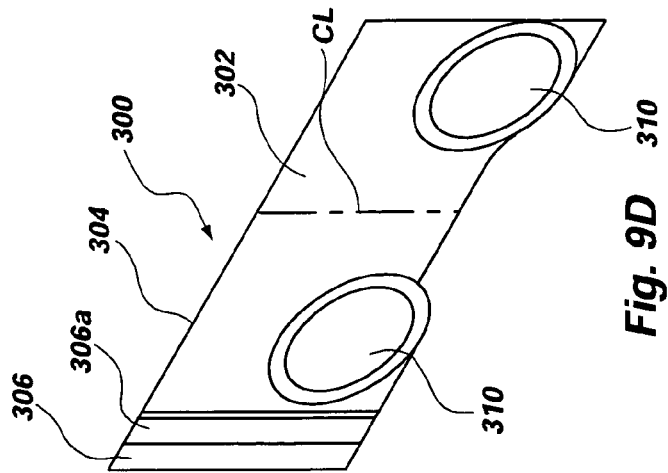
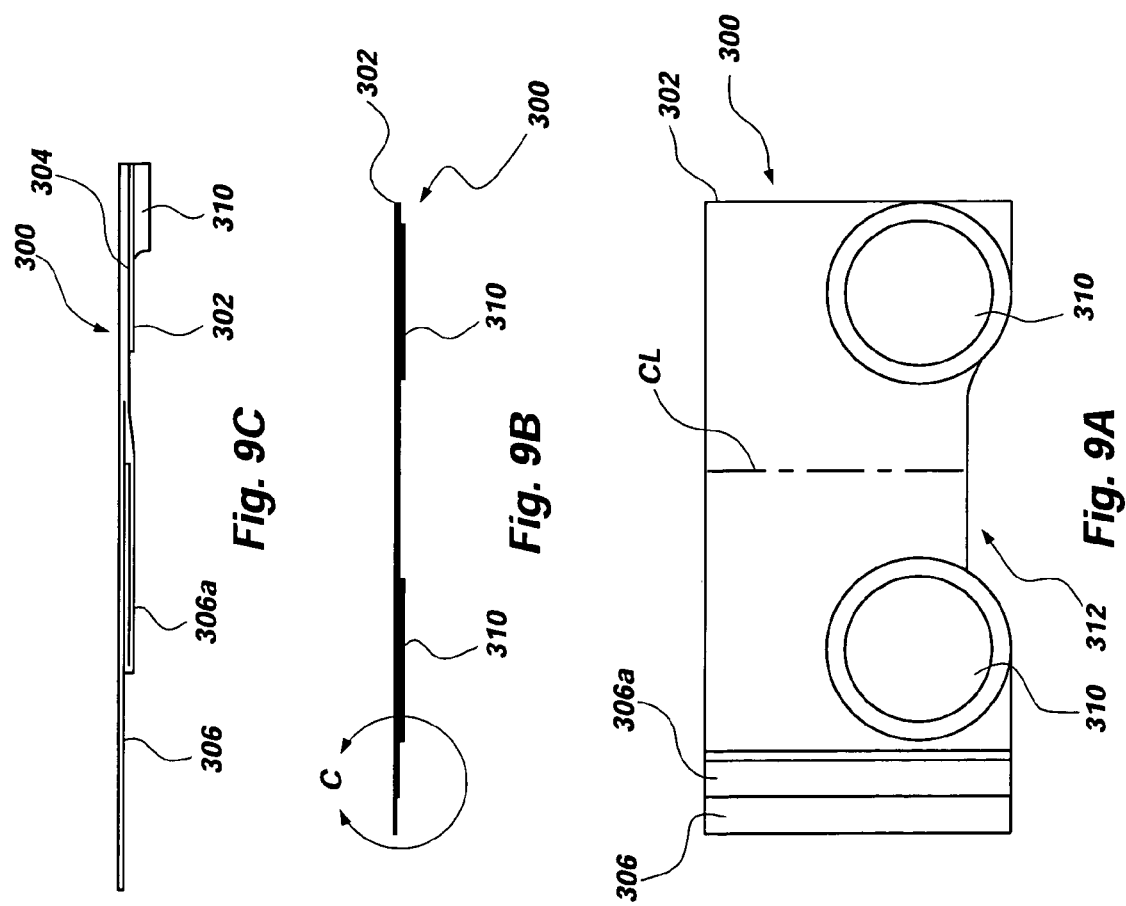
Fig. 9D
Fig. 9C
Fig. 9B
Fig. 9A

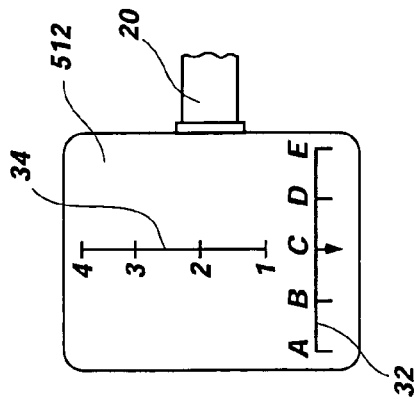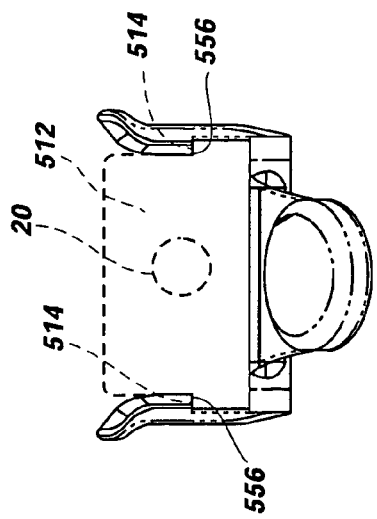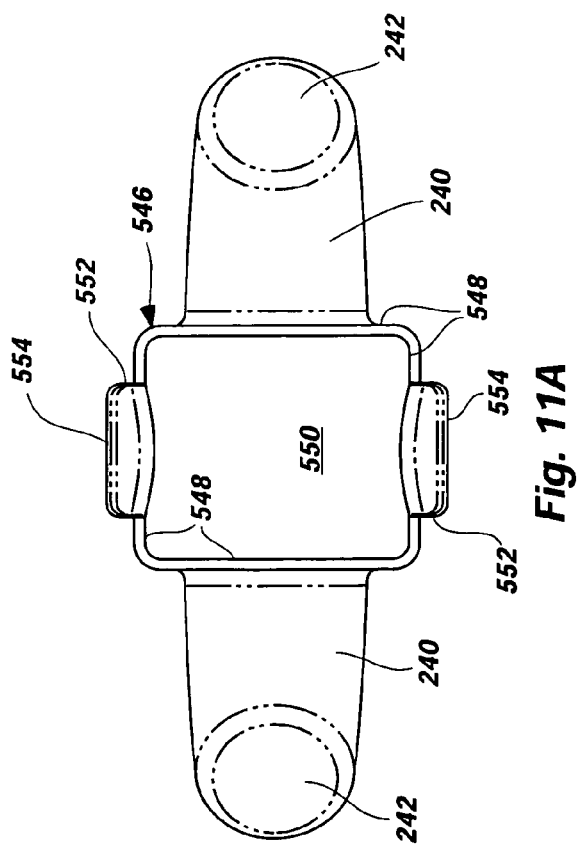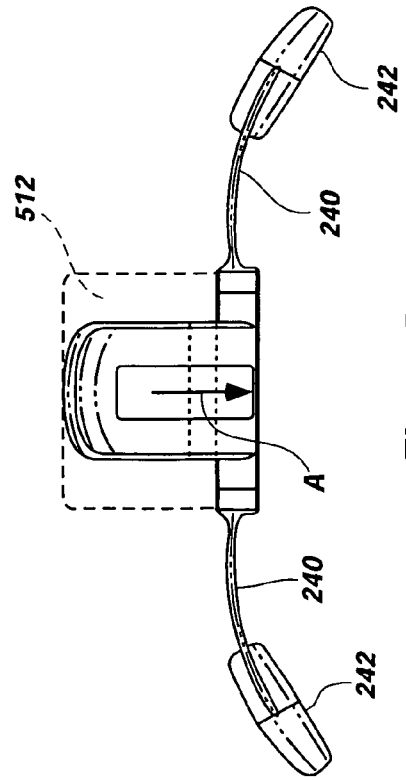

MULTIPLANAR ULTRASONIC VASCULAR SENSOR ASSEMBLY AND APPARATUS FOR MOVABLY AFFIXING A SENSOR ASSEMBLY TO A BODY

CROSS-REFERENCE TO RELATED APPLICATIONS

This application is a continuation-in-part of application Ser. No. 10/911,860, filed Aug. 3, 2004, pending, which is a continuation of application Ser. No. 10/872,699, filed Jun. 21, 2004, now U.S. Pat. No. 7,214,191, issued May 8, 2007, which is a divisional of application Ser. No. 10/072,662, filed Feb. 5, 2002, now U.S. Pat. No. 6,755,789, issued Jun. 29, 2004.

BACKGROUND OF THE INVENTION

1. Field of the Invention

This invention relates generally to the cannulation of veins and arteries under the guidance of ultrasound.

2. State of the Art

Insertion of catheters into central veins or arteries can be a difficult task because the vein or artery may be located deep within the body or may otherwise be difficult to access in a particular patient. Multiple attempts at penetration may result in extreme discomfort to the patient and loss of valuable time during emergency situations. Furthermore, central veins and arteries are often in close proximity to each other. While attempting to access the internal jugular vein, for example, the carotid artery may instead be punctured, resulting in severe complications or even mortality due to consequent blood loss due to the high pressure of the blood flowing in the artery.

To prevent complications during catheterization, it is known that ultrasonic instruments can be used to determine the location and direction of the vessel to be penetrated. Various approaches use a Doppler-only technique with no imaging. One such technique transmits ultrasonic waves via a transducer from the skin surface to the vessel. Due to the flow of blood in the vessel, or the pulsation of the vascular walls, the ultrasonic wave undergoes a Doppler shift effect, which causes the reflected signal to be at a frequency different from the transmitted signal. The frequency difference between the transmitted and received signals is then converted to an electrical signal, amplified and sent to an audio speaker. The frequency of the tone emitted from the speaker increases as the frequency difference becomes greater, indicating the approximate location of the vessel. Improvements to this technique place either the transmitting transducer, receiving transducer, or both transmitting and receiving transducers within a hollow needle, so that the audio signal becomes louder as the needle is turned toward a vessel within the patient's body. While such applications are helpful in guiding the needle toward the general location of vessels, the obtainable accuracy is obviously limited. Other limitations of this technology include difficulty distinguishing veins from nearby arteries, difficulty determining when the vessel has been penetrated, and difficulty implementing the known Seldinger technique.

Other conventional approaches to identification of vessel location and direction use two-dimensional ultrasound imaging to either mark the vessel location on the skin before attempting to access the vessel, using the known Seldinger technique, or view the vessel as the needle tip advances toward it. See *British Journal of Anaesthesia*, 822-6 (1999). However, it would be desirable to improve ultrasound imaging techniques for the cannulation of blood vessels to make the use of such technology less cumbersome and more accurate.

BRIEF SUMMARY OF THE INVENTION

The present invention uses ultrasound techniques in an improved method and apparatus for cannulation of blood vessels. In contrast to conventional approaches, the present invention provides a clinician with the ability to manipulate the needle during insertion with both hands while observing the progress of the needle toward and into the desired target vessel in substantially real time.

The apparatus of the invention comprises a sensor assembly including two ultrasonic, linear transducer arrays, each comprising a plurality of active imaging transducer elements, the arrays being oriented perpendicularly to each other to form a "T" configuration and carried by a housing. The 90° relative orientation of the array axes provides the ability to quickly and easily image blood vessels in both the longitudinal and transverse planes as a needle with attached catheter is guided toward a target vessel. One advantage of the present invention is that the needle operator may accurately orient the needle with respect to the target vessel and may, as desired, monitor the needle at all times as it passes through the anterior wall of the vessel. Thus, this technique and apparatus may eliminate the need to insert the first, or seeker, needle used in the Seldinger technique and greatly increase the accuracy over Doppler-only techniques where the needle operator is guided solely by an audible tone. Again, it is notable that the clinician employing the present invention is enabled to manipulate the needle during insertion with both hands while simultaneously observing the progress of the needle toward and into the desired target vessel.

In other embodiments of the present invention, the sensor assembly may be used in combination with a protective sheath having a frame element associated therewith and a cover configured to encompass the sensor assembly and bearing graphics to provide means, in cooperation with the frame element, for orienting the sensor assembly and securing the sensor assembly to the patient's body in a desired orientation.

In still another embodiment of the invention, the sensor assembly may include a housing configured to include two laterally extending protrusions or "wings" proximate the lower edges of two opposing side walls, the wings each carrying a magnet thereon. This embodiment of the sensor assembly may be employed in combination with a reference location element in the form of a dielectric (such as a polymer) film or tape bearing an adhesive on one side thereof for attachment to the skin of a patient over the general location of the blood vessel to be cannulated, the tape including two laterally spaced shims of a magnetically responsive metal or polymer. The lateral spacing of the shims approximates that of the magnets, but the shims are somewhat larger than the magnets to permit the sensor assembly to be moved about by the clinician over a limited area of the patient's body with respect to the film to precisely locate the sensor assembly. The magnets, in turn, permit such movement but exhibit magnetic fields robust enough to maintain the sensor assembly in place when it is released by the clinician.

In a variation of the foregoing embodiment, the sensor assembly housing may be configured to be received in a frame element having two laterally extending protrusions or "wings" proximate lower edges of two opposing side walls of the frame element, the wings each carrying a magnet thereon.

The aforementioned reference location element, having magnetically responsive shims, may be employed in cooperation with the frame element.

In still a further embodiment of the invention, the housing of the sensor assembly may be configured for use with a reference location element in the form of an elongated ribbon having an adhesive coating at each end thereof, the ribbon being adhered to the skin of the patient. The ribbon extends through a slot in the sensor assembly housing, which has associated therewith at least one resilient gripping element which may be manipulated by the clinician to release tension on the ribbon to enable sliding of the sensor assembly therealong as well as limited rotation thereof with respect to the ribbon to precisely locate the sensor assembly. When a desired location of the sensor assembly is reached, then the at least one resilient gripping element is released and the sensor assembly is fixed in place.

In further embodiments of the present invention, the sensor assembly further includes at least one ultrasonic Doppler transducer element used to transmit and receive a single ultrasonic beam at an angle relative to the imaging transducer array in the longitudinal plane. The addition of the Doppler transducer element, or elements, provides directional blood flow and blood velocity information with regard to the target vessel and others nearby and thus improves the ability to distinguish veins from arteries. The directional information from the Doppler transducer element or elements may be converted to a color mark with one distinct color indicating blood flow in one direction and another distinct color indicating blood flow in the opposite direction. For example, when the sensor housing is appropriately aligned on the body with respect to cover markings depicting blood flow toward and away from the heart, blood flow toward the heart may be indicated with the color blue and blood flow away from the heart may be indicated with the color red. Thus, when the single color scan line is overlaid on top of a grayscale longitudinal image of a possible target vessel on a monitor screen, a blue mark on the color screen will indicate a vein and a red mark will indicate an artery. While an array of Doppler elements may also be used to provide a full-color image, a single Doppler beam reduces the complexity and cost of providing desired directional flow information.

In still another embodiment, the Doppler transducer element or elements carried by the sensor housing may be configured to transmit and receive "chirped" ultrasound pulses to obtain Doppler information at discrete depths within the body. A pulse is chirped if its carrier frequency changes with time. This frequency modulation, or frequency sweeping, causes the Fourier spectrum of the chirped pulse to broaden. Thus, a digital signal processor may be used to analyze the reflected signal via a Fast Fourier Transform ("FFT") algorithm to separate distances or depths of various features within the body. The phase change between transmitted and received signals is used to determine speed and direction of flow in the blood vessels.

In yet another embodiment, two pulsed Doppler elements may be used for determining speed and direction of flow in the blood vessels. In this embodiment, the two pulsed Doppler elements each comprise a group of active imaging transducer elements included in one of the linear ultrasonic transducer arrays, specifically the array hereinafter termed a "longitudinal" array, which is to be positioned in use over the vessels to be detected and substantially parallel thereto. The two pulsed Doppler elements, each comprising a contiguous group of active imaging transducer elements, are mutually spaced from each other along the length of the array and are each angled at the same but relatively opposing angle to a perpendicular to the plane of the array of which they are a part. The two pulsed Doppler elements each transmit and receive ultrasonic signals, by which blood flow direction and velocity may be determined.

Yet another aspect of the present invention comprises a protective sheath into which the sensor assembly may be inserted, a packaging configuration therefor and a method of use thereof. The protective sheath comprises an elongated tubular thin polymer film element, closed at one end and open at the other. The protective sheath may be tapered so as to be of larger diameter or transverse dimension at the open end than at the closed end thereof. The open end of the protective sheath is folded back over the rest of the protective sheath so that a portion comprising about one-half of the protective sheath is inside-out, or everted, and extends over the remaining portion thereof. The end of the now-everted protective sheath, now open and defining a bore extending to the closed end of the sheath (the original or first open end of the protective sheath now lying adjacent and surrounding the original closed end due to eversion), is rolled outwardly back upon itself toward the closed end until only a small "pouch" or "foot" of a size suitable for receiving the sensor assembly remains, the doubled and rolled polymer film forming a toroidal shape defining a mouth of the pouch or foot. At that juncture, the skirt of material defining the now-everted original or first open end of the protective sheath is folded back over the outside of the toroidal shape of rolled polymer film. In use, the inventive protective sheath may be placed in a tray of a kit including other sterile, disposable elements of the present invention with its mouth defined by the skirt and toroidal shape of rolled polymer film facing upward. In use, the sensor assembly (which is not sterile) may be placed into the pouch or foot through the mouth and the folded-back skirt of the protective sheath, grasped and pulled proximally along the cable extending to the sensor assembly to maintain sterility of the exterior of the protective sheath while encompassing the nonsterile sensor assembly and associated cable therein for use. Tabs of another material may be secured to the skirt to facilitate visual identification and grasping of the skirt.

Methods of vessel identification, a system incorporating the sensor housing of the present invention and a kit of disposable sterile components are also encompassed by the present invention.

BRIEF DESCRIPTION OF THE SEVERAL VIEWS OF THE DRAWINGS

FIGS. 8A through 8D respectively comprise a top elevation, a frontal elevation, a side elevation and a perspective view of another exemplary implementation of a sensor assembly according to the present invention for use with a magnetic reference location element;

FIGS. 9A through 9D respectively comprise a top elevation, a frontal elevation, an enlargement of a portion of the frontal elevation and a perspective view of a magnetic reference location element suitable for use with the sensor assembly embodiment of FIGS. 8A through 8D.

FIGS. 11A through 11C respectively depict top, frontal and side elevations of a frame element configured to receive a housing of a sensor assembly of the present invention; and FIG. 12 comprises a top elevation of a sensor assembly housing configured to be received within the frame element.

DETAILED DESCRIPTION OF THE INVENTION

Figure 1A:
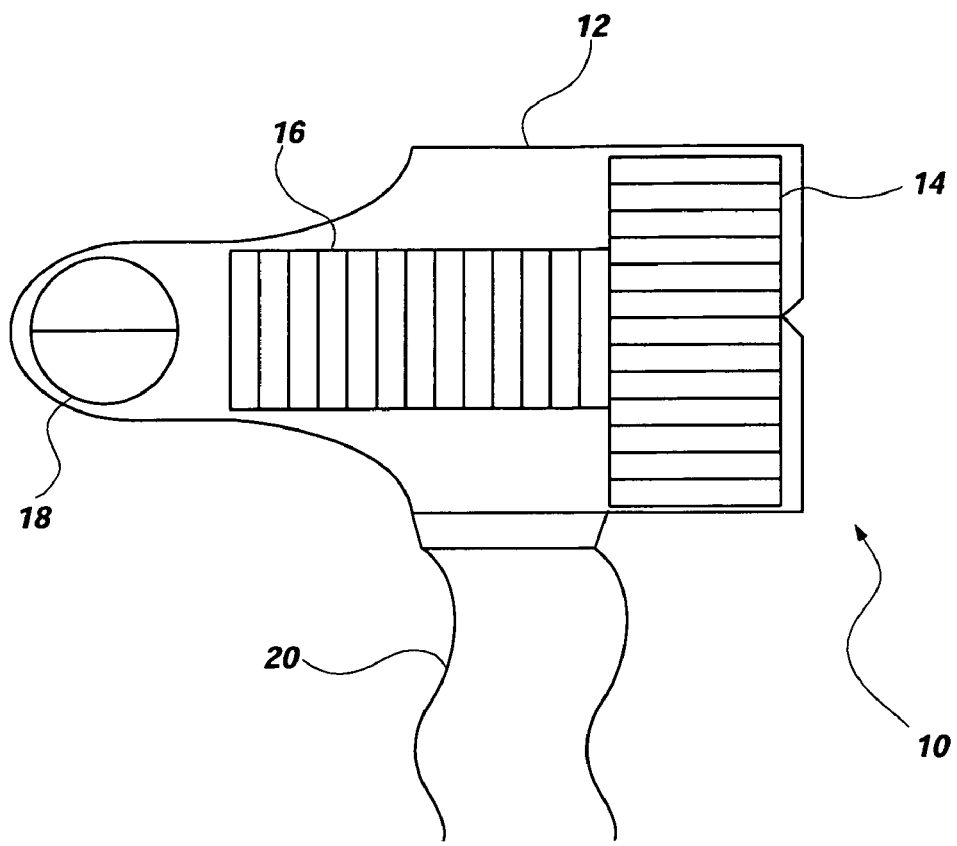
FIGS. 1A and 1B respectively comprise a bottom schematic view and a side schematic view of a first exemplary sensor assembly of the present invention.
Figure 1B:
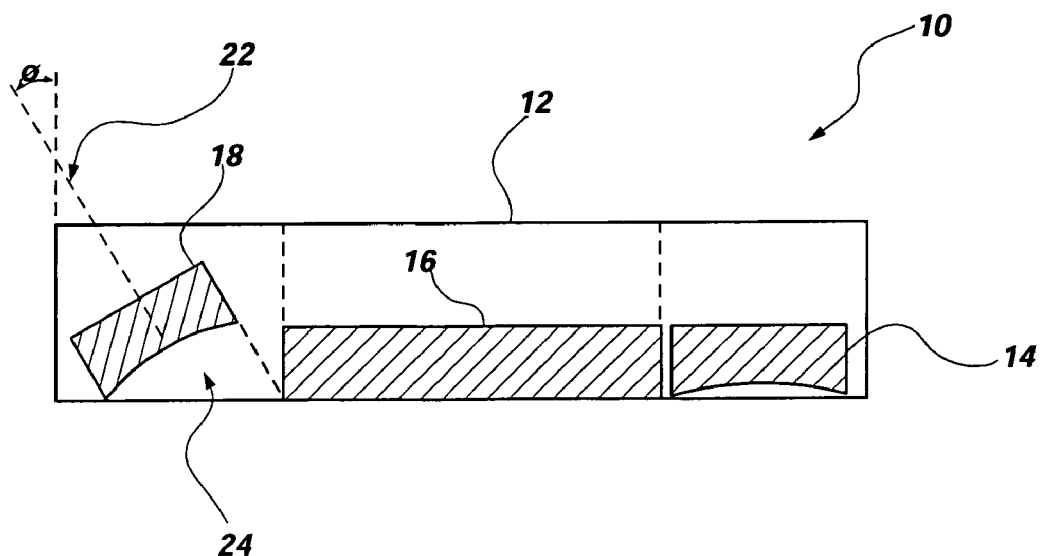

FIGS. 1A and 1B comprise a schematic illustration of a sensor assembly 10 in accordance with the present invention. The sensor assembly 10 includes a housing 12 containing a first linear, ultrasonic elongated cross-sectional or transverse transducer array 14 and a second linear, ultrasonic elongated longitudinal transducer array 16; transducer arrays 14 and 16 are placed perpendicular to one another. Transducer arrays 14 and 16 as assembled with housing 12 form a "T" shape and are employed to obtain ultrasonic images of potential target blood vessels simultaneously in both the transverse and longitudinal planes. Transverse transducer array 14 defines the head of the T, while longitudinal transducer array 16 defines the body thereof. Transducer arrays 14 and 16 each extend linearly and include a plurality of mutually adjacent piezoelectric active imaging transducer elements for transmitting and receiving ultrasonic waves, as will be understood by one having skill in the field of the present invention. However, while the two linear transducer arrays 14, 16 are described and depicted as arranged in a T configuration, it is contemplated that any arrangement placing transducer arrays 14, 16 in mutually perpendicular relationship is suitable and encompassed by the present invention.

In addition to transducer arrays 14 and 16, one embodiment of the apparatus of the present invention includes a "chirped" Doppler transducer element 18 for transmitting and receiving a single ultrasonic Doppler beam 22 in alignment with the longitudinal transducer array 16 and at incident angle φ, for example, about 20° to about 30°, perpendicular to the patient's skin underlying housing 12. The Doppler transducer element 18 provides blood flow direction and velocity information as an additional feature to aid the clinician in distinguishing veins from arteries during cannulation. The Doppler transducer element 18 includes one semicircular piezoelectric transmitter Tx for generating the Doppler beam 22 and one semicircular piezoelectric receiver Rx for receiving the reflected Doppler beam 22. The orientation and relative alignments of Tx and Rx may be as shown in FIG. 1A, or rotated ±90° or ±180°, as desired. Alternatively, if a "pulsed" Doppler transducer element is employed, only a single circular combination emitter and receiver element is required. Further, while Doppler transducer element 18 is shown as having a concave face in FIG. 1B, a planar or convex face is also suitable. An attached ultrasonic lens may also be employed. It will be readily recognized that while multiple transmitters and receivers may be employed to acquire Doppler information corresponding to the entire ultrasound scan and image produced by longitudinal transducer array 16, using a single beam to produce Doppler information corresponding to a single scan line traversing the target blood vessel will provide all required directional blood flow information necessary for safe vessel cannulation and at far less complexity and cost.

By way of example only, manufacturers of custom medical grade transducers, such as may be suitable for use in implementing the present invention, include Acoustic Imaging Transducers of Phoenix, Ariz.; Krantkramer of Lewistown, Pa.; and Blatek, Inc. of State College, Pa.

The sensor assembly 10 of the present invention further includes a multi-conductor cable 20, which enters housing 12 at one side thereof and is operably coupled to the cross-sectional on transverse transducer array 14, the longitudinal transducer array 16, and the Doppler transducer element 18. Also, in order to increase the efficiency of the Doppler transducer element 18 and to reduce reflections in gap area or cavity 24 created by incident angle φ of Doppler beam 22, gap area 24 may be filled with a material such as an epoxy or polymer, which is substantially acoustically matched to bodily tissue. Suitable compounds include, without limitation, PMMA, PTFE, and RTV silicone available, for example and not by way of limitation, from 3M Corporation, Minneapolis, Minn., and DuPont, Wilmington, Del. Of course, gap area or cavity 24 may also be filled with an acoustic transmission gel, or be partially filled with an epoxy or polymer and partially filled with an acoustic transmission gel.

Figure 2:
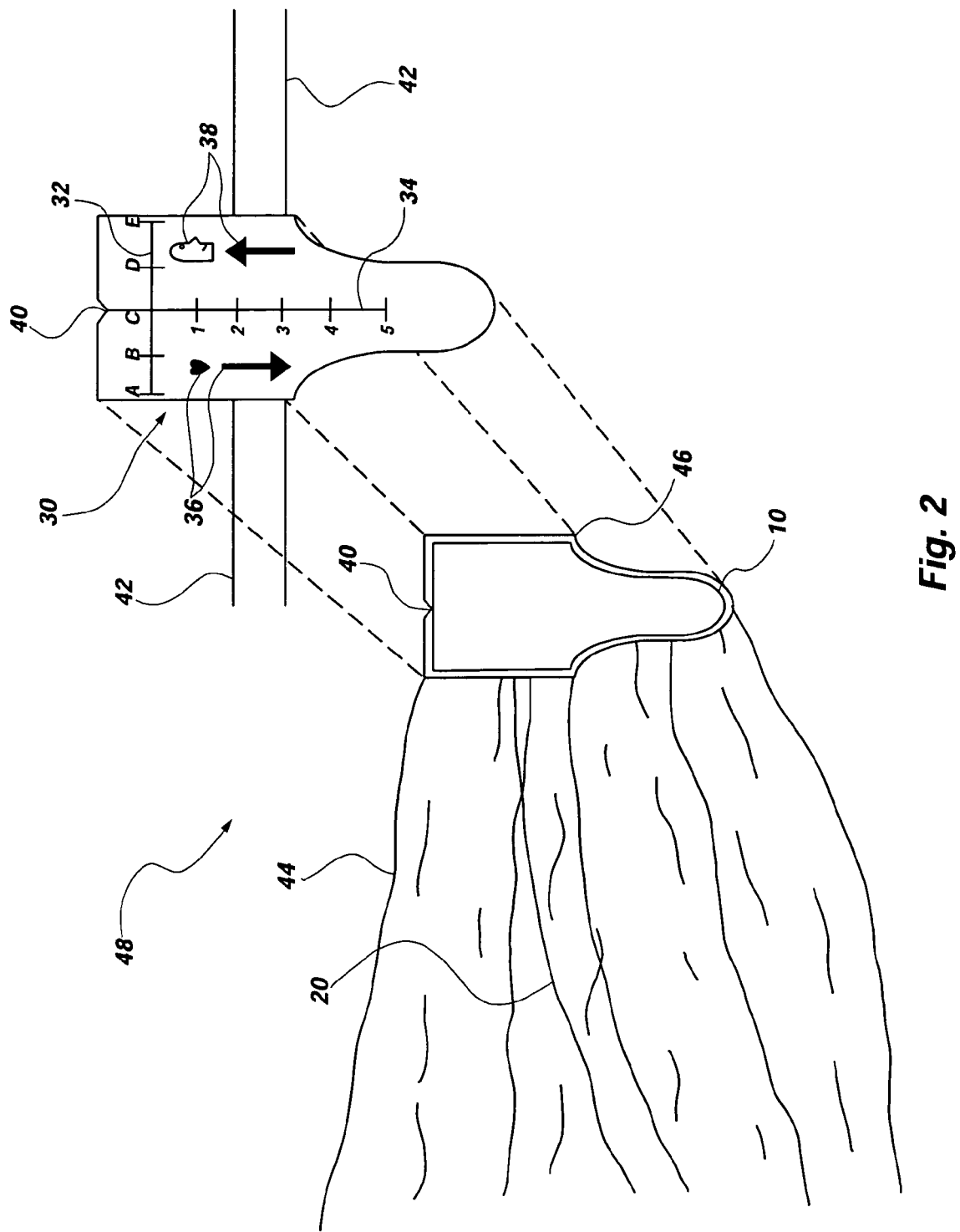
FIG. 2 is an exploded schematic view of the sensor assembly of FIGS. 1A and 1B disposed within a transparent, protective sheath and with a housing cover according to the present invention.
Figure 3:
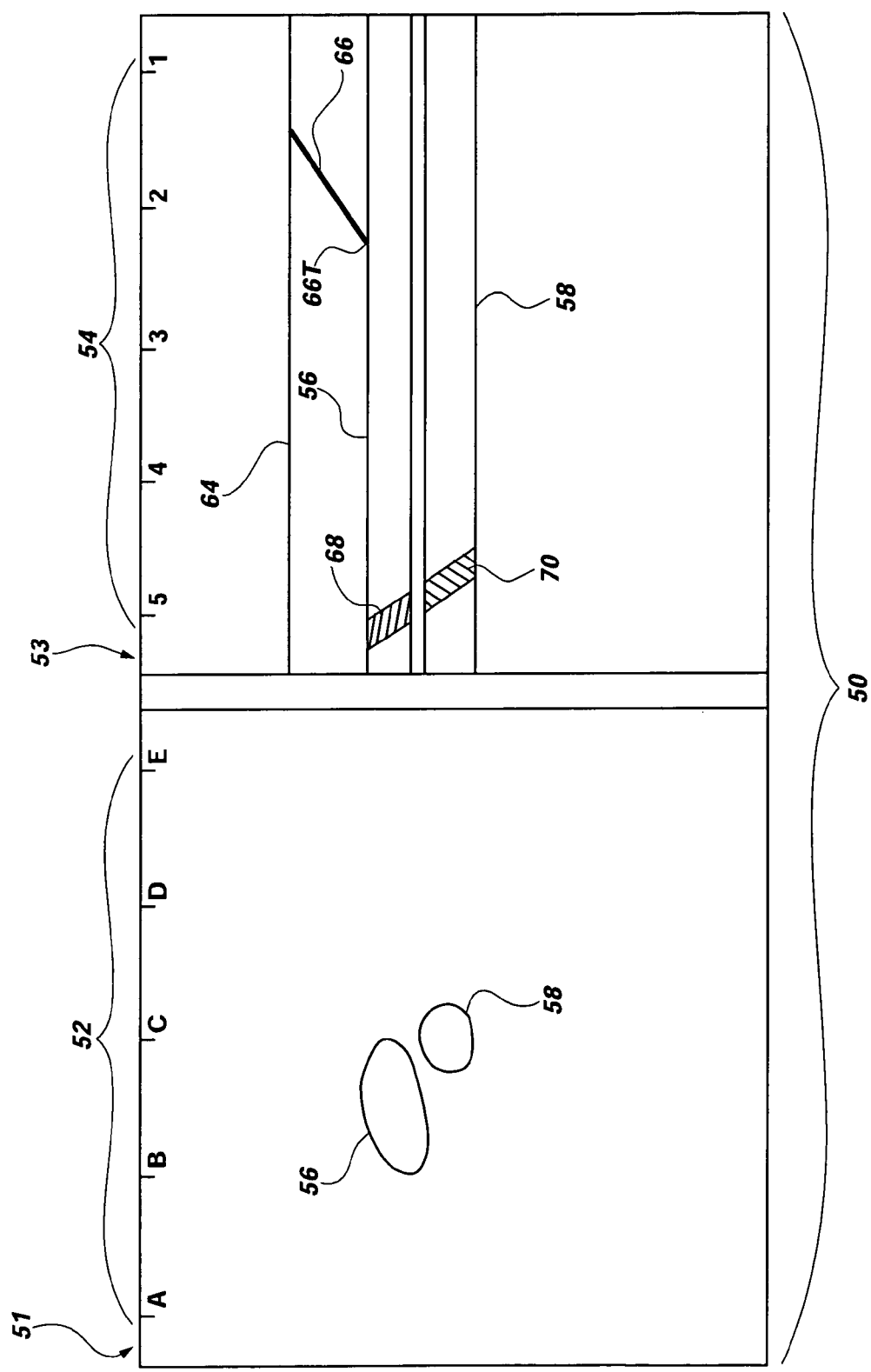
FIG. 3 comprises an exemplary dual-panel ultrasound image provided by the apparatus of the present invention of a patient's neck in two imaging planes as a needle is guided toward the internal jugular vein for cannulation.

FIG. 2 and FIG. 3 below illustrate a first, schematically illustrated, exemplary sensor assembly according to the present invention in the context of a technique for using the present invention for cannulation of the internal jugular vein located in the neck of a human patient. However, it will be apparent that the apparatus and method described may also be used to identify and access various blood vessels within a mammalian subject's body. FIG. 2 is a schematic illustration of the sensor assembly 10 as described with reference to FIGS. 1A and 1B and as viewed from above looking down on cover 30 in use with an elongated, flexible, protective and preferably transparent sheath 44 and a reference location element in the form of an elongated ribbon 42 bearing an adhesive at each end thereof to form an ultrasonic cannulation assembly 48. Cover 30 is graphically marked and configured to aid in the use of the sensor assembly 10 for the cannulation of blood vessels. The elongated, flexible, protective, transparent sheath 44 provides a protective enclosure for the sensor assembly 10 for use in a sterile field within an operating room. One suitable elongated, flexible, protective, transparent sheath 44 for use with the present invention is offered commercially by Protek Medical Products, Inc. of Iowa City, Iowa, while another, more preferred embodiment of protective, transparent sheath 44 is described herein.

In this embodiment, the elongated, flexible, protective, transparent sheath 44 extends from a relatively larger, open end to a relative smaller, closed end to form a tapered, flaccid and thus highly flexible tubular enclosure with a frame element 46 bonded to the interior surface of the narrower, closed end thereof. The elongated, flexible, protective, transparent sheath 44, cover 30, and adhesive ribbon 42 comprise a disposable kit of sterile components for use with this embodiment of the invention and are discarded once each cannulation procedure is complete. The sensor assembly 10 may thus be reused without sterilization for new procedures with a new kit of disposable items including the protective, transparent sheath 44, cover 30, and adhesive ribbon 42.

Prior to use, conventional acoustic transmission gel is placed inside the elongated, flexible, protective, transparent sheath 44 within the area defined by the frame element 46 to provide efficient acoustic coupling between the material of the transparent sheath 44 and the sensor assembly 10 secured to the frame element 46. After disposition of the acoustic gel, the sensor assembly 10 is inserted into the protective, transparent sheath 44 and housing 12 snapped into the frame element 46, the multi-conductor cable 20 being aligned with the longitudinal axis of the elongated, flexible, protective, transparent sheath 44 and extending to and through an opening at the opposite, wider end thereof for connection to a monitoring device. Next, the cover 30 is placed over the housing 12 of sensor assembly 10 from the exterior of the protective, transparent sheath 44 and then engaged with the frame element 46 to tighten the cover 30 over the sensor assembly 10. After applying additional acoustic transmission gel to the patient's skin in the area to be accessed, the ultrasonic cannulation assembly 48 is placed on the patient's body in order to obtain ultrasound images of a target blood vessel.

Cover 30 bears orientation markings on its exterior surface indicating blood flow toward the heart 36 and away from the heart 38 to assist in proper orientation of sensor assembly 10 on the patient's body. For example, if attempting to cannulate the internal jugular vein of the neck, the sensor assembly 10 of the ultrasonic cannulation assembly 48 would be placed on the patient's neck with the arrow depicted in orientation marking 36 pointing toward the patient's heart and the arrow depicted in orientation marking 38 pointing toward the patient's head. Proper orientation of the ultrasonic cannulation assembly 48 ensures that information concerning blood flow direction obtained from the Doppler transducer element 18 correctly indicates whether a potential target vessel is a vein or an artery.

Cover 30 also contains slots 35 (FIG. 4) through which the adhesive ribbon 42 may pass to secure the ultrasonic cannulation assembly 48 to the skin of the patient for hands-free operation thereof during the cannulation procedure. The adhesive ribbon 42 contains an area of adhesive material on the bottom (skin contact) side toward each end thereof, leaving the center region of the adhesive ribbon 42 free of adhesive material where it comes into contact with the ultrasonic cannulation assembly 48. A suitable adhesive is a 1526 tape adhesive offered by 3M Corporation, Minneapolis, Minn. Thus, after orienting the ultrasonic cannulation assembly 48 on the patient's body and obtaining an ultrasound image of the vessel to be accessed (see FIG. 3), the adhesive ribbon 42 is adhered to the skin at both sides of sensor assembly 10. Further, the cover 30 contains resilient, movable gripping elements, such as portions of a compressible spring clip (not shown in FIG. 2), extending about the sides thereof to grip the adhesive ribbon 42 when engaged therewith and create tension on both ends of the adhesive ribbon 42 to hold the ultrasonic cannulation assembly 48 tightly against the skin. Further, by disengaging the gripping elements, ribbon tension is released and the ultrasonic cannulation assembly 48 may be easily moved from side to side or rotated at a slight angle until the optimum ultrasound image is obtained, at which juncture the gripping elements are re-engaged with adhesive ribbon 42 to secure sensor assembly 10 in place.

Cover 30 bears transverse grid markings 32, longitudinal grid markings 34 and a notch-like needle guide 40, which are used in combination to help guide the needle toward the vessel to be accessed. The transverse grid markings 32 are aligned parallel to transverse transducer array 14 and centered with respect to the head of the T, while the longitudinal grid markings 34 are aligned parallel to longitudinal transducer array 16 and over the body of the T. The needle guide 40 is aligned longitudinally with the body of the T and is adjacent the head end thereof. The notch of the needle guide 40 is aligned with a like notch of the frame element 46 to allow clear passage of the needle to the skin tissue underlying sensor assembly 10 without perforation of elongated, flexible, protective, transparent sheath 44 and possible compromise of the sterile field. After the optimum ultrasound image of the vessel is obtained through manipulation of sensor assembly 10 secured to frame element 46 and within protective, transparent sheath 44 and the ultrasonic cannulation assembly 48 is secured to the patient as described above, a needle with catheter attached is inserted into the tissue at a location defined by the needle guide 40. The needle is then guided toward the target vessel location, which is visually ascertained in relation to transverse grid markings 32 comprising letters A through E and longitudinal grid markings 34 comprising numerals 1 through 5 as will be hereinafter described. The method of guiding the needle toward the vessel using grid markings 32 and 34 will become more apparent in the discussion of FIG. 3 which follows.

FIG. 3 is a representation of a dual-panel ultrasound image 50 generated by the monitoring system used with ultrasonic cannulation assembly 48 in the method of the present invention for the cannulation of blood vessels. The dual-panel ultrasound image 50 includes a transverse image 51 and a longitudinal image 53 of the neck displayed simultaneously in substantially real time on a single screen using known split-screen or picture-in-picture technology. The transverse image 51 is obtained from the transverse transducer array 14 of the sensor assembly 10 of FIGS. 1A and 1B and comprises a transverse image 51 of the internal jugular vein 56 and a transverse image 51 of the adjacent carotid artery 58. Also shown is a transverse grid display 52, which corresponds to the transverse grid markings 32 (letters A through E) on cover 30 of FIG. 2. Stated another way, transverse grid markings 32 are keyed to transverse grid display 52. The transverse grid display 52 and the transverse grid markings 32 indicate the relative location of the needle insertion point to the vessel to be punctured. For example, a needle inserted through the needle guide 40 of FIG. 2 would enter the tissue at a location proximate C relative to sensor assembly 10 on the transverse grid markings 32. However, FIG. 3 shows that the cross-sectional image of the internal jugular vein 56 is approximately laterally between B and C and that the cross-sectional image of the carotid artery 58 corresponds almost directly to C of the cross-sectional grid display 52. Therefore, in order to avoid the carotid artery 58 and access the internal jugular vein 56, the sensor assembly 10 would be moved laterally until internal jugular vein 56 is directly below C on cross-sectional grid display 52.

Similarly, the longitudinal image 53 is obtained from the longitudinal transducer array 16 of the sensor assembly 10 of FIGS. 1A and 1B and displays a longitudinal image of the internal jugular vein 56 and an image of the skin surface 64. If the carotid artery 58 is substantially directly below internal jugular vein 56, carotid artery 58 will also be shown, as depicted in FIG. 3. In addition, a needle image 66 may optionally be displayed to show the location of the needle tip 66T as it passes from the skin surface 64 through the tissue toward the longitudinal image of the internal jugular vein 56. Thus, the needle image 66 provides the clinician with a precise indication of impending needle entry through a vessel wall. The imaging method may be used with a needle designed to enhance the image of the needle tip 66T by plating or otherwise treating the needle tip surface with a material that is highly reflective of ultrasonic waves, such needles being known in the art and being termed "echogenic." One such needle employs a tip dipped in a polymer, including gas bubbles therein, providing a diffuse rather than specular reflection. Also shown is a longitudinal grid display 54, which corresponds to the longitudinal grid markings 34 on cover 30 of FIG. 2. Stated another way, longitudinal grid markings 34 are keyed to longitudinal grid display 54. The longitudinal grid display 54 and the longitudinal grid markings 34 indicate the relative longitudinal location of the needle to the target blood vessel as it passes through the tissue under sensor assembly 10 in a manner analogous to the example above for the transverse grid display 52 and the transverse grid markings 32.

FIG. 3 also includes an example of how blood flow information is indicated to the user of the preferred embodiment of the present invention. As discussed above, the Doppler transducer element 18 of FIGS. 1A and 1B provides blood flow information to help distinguish veins from arteries within a patient's body. In FIG. 3, blood flow direction indicators 68 and 70 represent a means of providing visually perceptible indicia to identify blood flow direction in correspondence with longitudinal image 53. In the embodiment of FIGS. 1A and 1B, a single scan line of Doppler information obtained from the Doppler transducer element 18 is overlaid on top of the longitudinal image 53. The preferred method of distinguishing blood flow direction between two potential target vessels, one direction of blood flow depicted by indicator 68 and blood flow in the opposite direction depicted by indicator 70, is to display indicators 68 and 70 in two distinctly different colors. For example, a color coding scheme may be defined such that deoxygenated blood flow in veins corresponds to the color blue and oxygenated blood flow in arteries corresponds to the color red. Thus, blood flowing toward the heart in the longitudinal image of the internal jugular vein 56 could be indicated by displaying indicator 68 in blue while blood flowing toward the head in the longitudinal image of the carotid artery 58 could be indicated by displaying indicator 70 in red. This color coding scheme is also carried over to the orientation markings 36 and 38 on cover 30 of FIG. 2. Thus, in the present example, orientation marking 36 would be blue to further indicate blood flowing toward the heart and orientation marking 38 would be red to further indicate blood flowing toward the head. The inventors recognize that any combination of colors, including variations in gray-scale shading, may be used to indicate blood flow direction and such variations are encompassed by the present invention. Further, it is recognized that many other methods of indicating blood flow direction may be used including, but not limited to, displaying on transverse image 51 or longitudinal image 53 symbols, patterns, letters, or words corresponding to distinct blood flow directions. Also, blood flow direction may be indicated for the sake of simplicity by displaying only one indicator corresponding to either blood flow toward or away from the heart. Blood flow velocity may also be calculated from the signals sent and received by Doppler transducer element 18.

Figure 4:
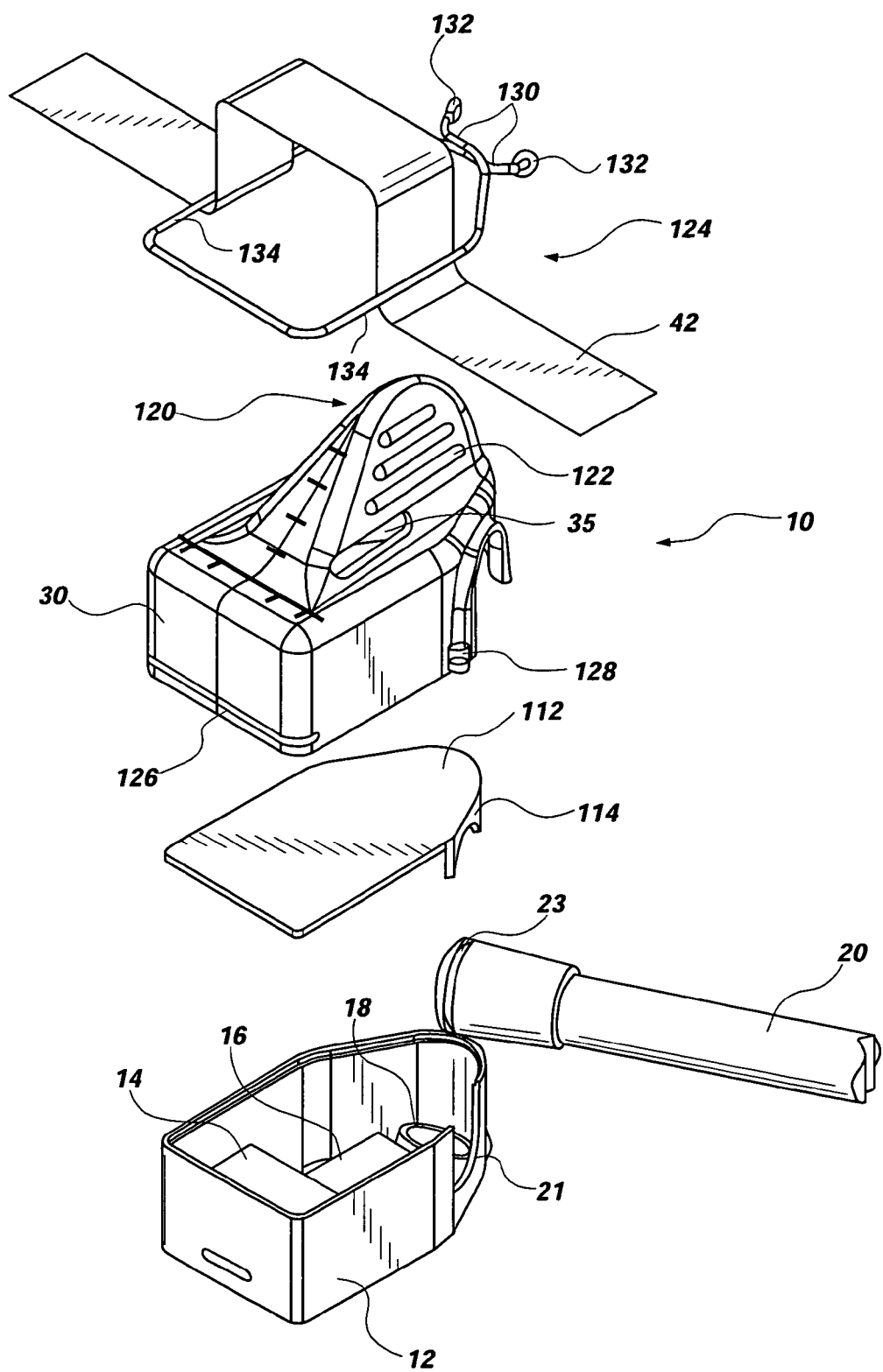
FIG. 4 comprises an exploded, detailed view of one exemplary implementation of a sensor assembly of the present invention employed in combination with a ribbon-type reference location element.

FIG. 4 depicts a more detailed implementation of the sensor assembly 10 depicted in FIGS. 1A, 1B and 2. Elements and features previously identified with respect to FIG. 2 are identified by the same reference numerals in FIG. 4. Linear transducer arrays 14 and 16 and Doppler transducer element 18 are shown disposed in housing 12, multi-conductor cable 20 entering housing 12 through a cutout 21 in the sidewall thereof. An array housing lid 112 having protrusion 114 secures the end of multi-conductor cable 20 in cooperation with cutout 21, the sidewall of the housing 12 and the protrusion 114 gripping multi-conductor cable 20 in annular slot 23. Cover 30, also termed a "shell," is configured to conformally extend over housing 12 and the bottom end thereof is configured to engage frame element 46 (not shown in FIG. 4) in a snap-fit fashion, housing 12 being trapped therebetween. Riser 120 extends upwardly from the main body of cover 30 and includes a plurality of gripping elements 122 on each side thereof to assist gripping of riser 120 by the fingers of the clinician. Slots 35 extend through each side of riser 120, and adhesive ribbon 42 (shown above cover 30 in FIG. 4 for clarity) extends through slots 35 and to either side of cover 30. A resilient gripping element in the form of spring clip 124 extends about the lower periphery of cover 30 in engagement with slots 126 and 128, the crossed ends 130 of spring clip 124 having loops 132. When in a relaxed position, the side rails 134 of spring clip 124 snugly clamp adhesive ribbon 42 against the sidewalls of cover 30. However, when loops 132 are pressed toward each other, as by using the thumb and forefinger, side rails 134 are pushed away from the sidewalls of cover 30, permitting sensor assembly 10 to be slid back and forth and rotated somewhat with respect to adhesive ribbon 42, the latter due to a slot elongation greater than the width of the adhesive ribbon 42.

Figure 5:
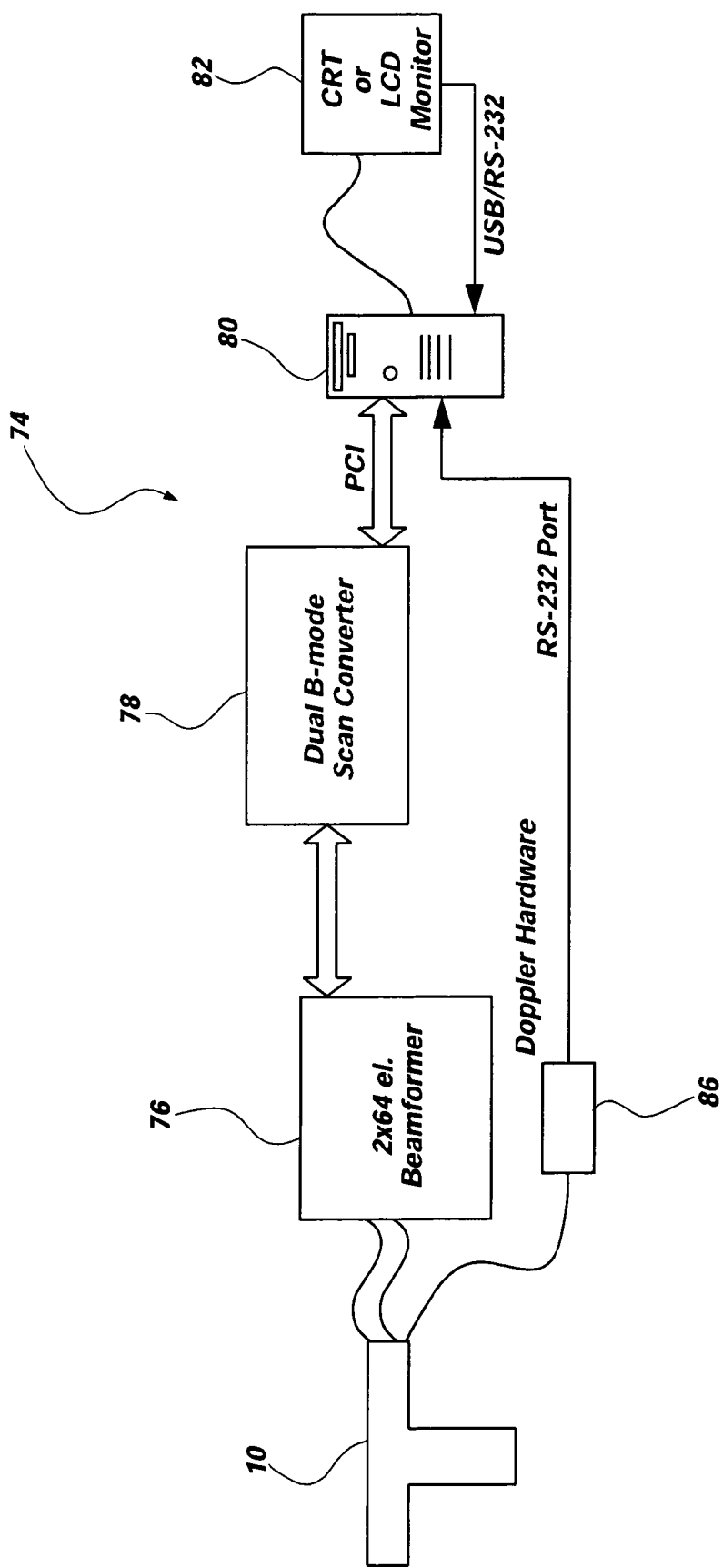
FIG. 5 is a block diagram of an exemplary system for the cannulation of blood vessels incorporating a sensor assembly of the present invention.

As shown in FIG. 5, a monitoring system 74 includes a multi-element ultrasonic beamformer (also termed "processing board") 76 and Doppler hardware 86 (see FIG. 6 for detail) of sensor assembly 10 operably coupled to the multi-conductor cable 20 of the sensor assembly 10 of FIGS. 1A and 1B. Further, the monitoring system 74 includes a dual B-mode digital scan converter 78 coupled to the beamformer 76, a suitably programmed host computer 80, such as a personal computer, and a display device 82, which may comprise a cathode ray tube (CRT) monitor. Other types of monitors, such as LCD touch screen monitors, or TFT monitors, may also be employed. Suitable beamformers and scan converter boards are available, for example, from B-K Medical of Copenhagen, Denmark; Analogic, Inc. of Peabody, Mass.; and Telemed of Vilnius, Lithuania.

By way of further exemplary detail, the housing 12 may define dimensions of (L×W×H) of 42 mm×21 mm×11 mm. A Zero Insertion Force (ZIF) connector is used to connect transducer arrays 14 and 16 to Doppler transducer element 18. Multi-conductor cable 20 comprises a one-centimeter-diameter cable which exits the side of the housing 12. The elongated transducer arrays 14 and 16 each comprise piezoelectric arrays, including sixty-four elements with an element pitch of 0.3 mm which operate at 7.5 MHZ. Focal depth is 20 mm (although a variety of focal lengths may be provided) and the elements possess about a 50-60% 6 dB bandwidth. Doppler transducer element 18 is also piezoelectric, includes a piezoelectric transmitter Tx and a piezoelectric receiver Rx and operates at 5 MHZ, possessing greater than a 75% 6 dB bandwidth. A single piezoelectric element performing as both a transmitter and receiver may also be used. The diameter of the combined transmitter and receiver is 8 mm, and the focal depth is 20 mm (although, again, a variety of focal lengths may be provided). Doppler transducer element 18 is oriented in housing 12 such that incident angle φ of Doppler beam 22 is 30°.

The dual B-mode digital scan converter 78 takes image information from the beamformer 76 via a 34-pin ribbon cable and displays the information on display device 82 in substantially real time. By "substantially real time," it is meant that image data from one array will be interleaved by host computer 80 with data from the other array and displayed simultaneously in a dual-panel, split-image format at 10-20 frames per second per image.

The host computer 80 may comprise a specifically packaged personal computer having the ability to run a MICROSOFT WINDOWS® operating system, as well as appropriate ultrasound imaging software. The software is preferably stored on a solid-state drive (Disk on Chip) as opposed to a conventional disc drive, in order to facilitate the boot-up and boot-down processes. It is currently believed that the minimum hardware requirements for host computer 80 include a Pentium 133 MHZ or better processor, 32 MB of DRAM, 128 MB hard disk capacity, one RS-232 port, PCI Bus interface ports and a compatible video card, many of which are commercially available from multiple sources.

Figure 6:
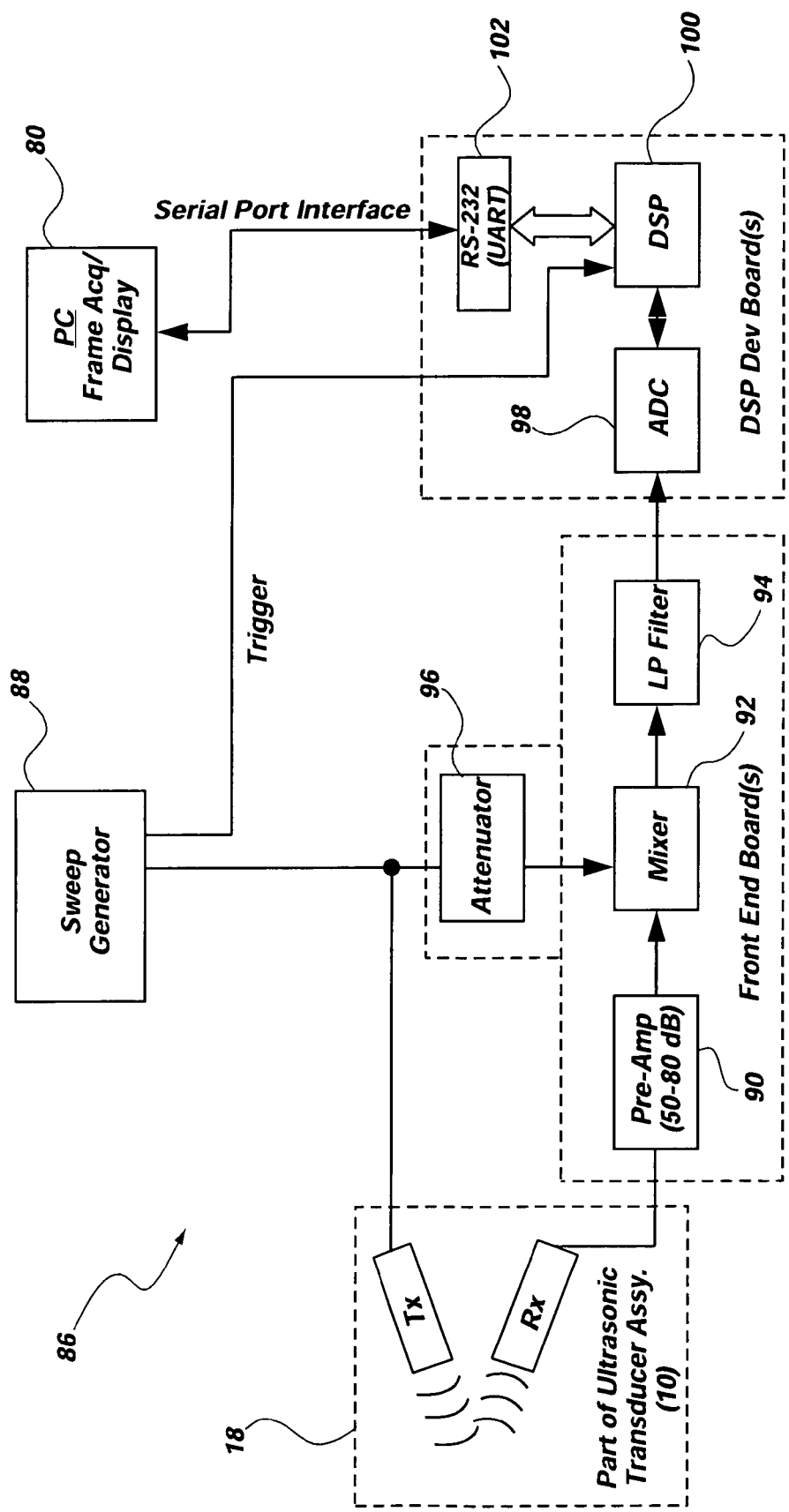
FIG. 6 is a block diagram of one embodiment of exemplary Doppler processing hardware for "chirped" Doppler suitable for use in the system of FIG. 5.

As shown in FIG. 6, chirped Doppler hardware 86, if used in the system of FIG. 5, includes a pre-amplifier 90 coupled to the Doppler transducer element 18 of FIGS. 1A and 1B, a mixer 92, a low-pass filter 94, an analog-to-digital converter ("ADC") 98, a digital signal processor ("DSP") 100, a serial communication device 102 for interfacing the DSP 100 to the host computer 80 of FIG. 5, a sweep generator 88 coupled to the Doppler transducer element 18 of FIGS. 1A and 1B and an attenuator 96. The Doppler transducer element 18 may, as previously noted, employ chirped Doppler hardware 86 to convert depth information into the frequency domain, allowing the user to obtain Doppler information at discrete depths which correspond to discrete frequency "bins." Alternatively, a conventional pulsed Doppler technique may also be employed. Data gathered by Doppler transducer element 18 is coded into a bit vector and sent over an RS-232 port to host computer 80 where the bit vector is converted to a color vector indicative of blood flow direction, which is overlaid on top of longitudinal image 53 generated by longitudinal transducer array 16 as processed by dual B-mode digital scan converter 78.

Figure 7A:
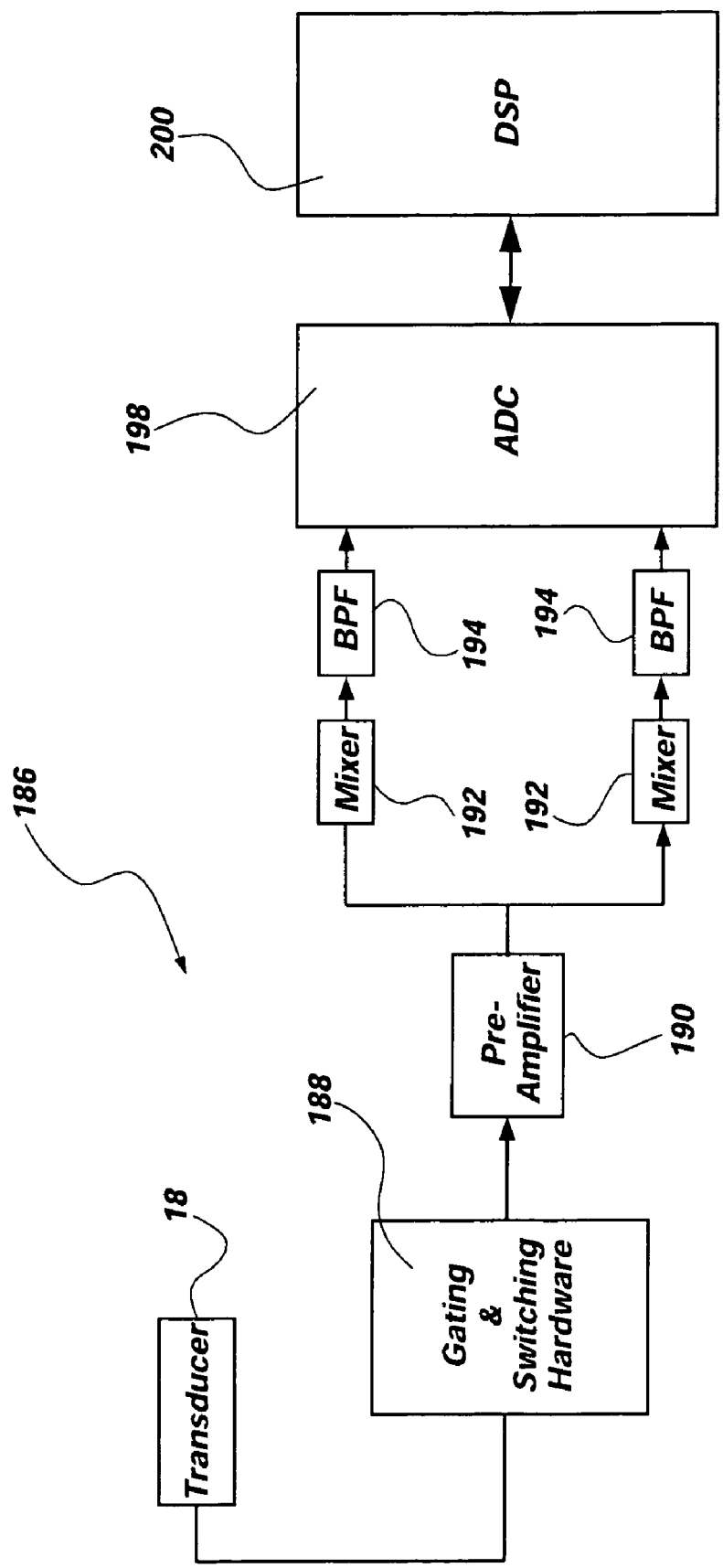
FIG. 7A is a block diagram of another embodiment of exemplary Doppler processing hardware for a first approach to "pulsed" Doppler suitable for use in the system of FIG. 5.

As shown in FIG. 7A, one embodiment of pulsed Doppler hardware 186, if used in the system of FIG. 5, includes gating and switching hardware 188 coupled to the Doppler transducer element 18 of FIGS. 1A and 1B and to a pre-amplifier 190, which, in turn, is coupled to dual mixers 192, each of which are coupled to band pass filters ("BPF") 194, these being coupled to an analog-to-digital converter ("ADC") 198, a digital signal processor ("DSP") 200 and a serial communication device 102 (see FIG. 6) for interfacing the DSP 200 to the host computer 80 of FIG. 5. The Doppler transducer element 18 may, as previously noted, employ pulsed Doppler to obtain Doppler information at discrete depths. Data gathered by pulsed Doppler transducer element 18 is coded into a bit vector and sent over an RS-232 port to host computer 80 where the bit vector is converted to a color vector indicative of blood flow direction, which is overlaid on top of longitudinal image 53 generated by longitudinal transducer array 16 as processed by dual B-mode digital scan converter 78.

Figure 7B:
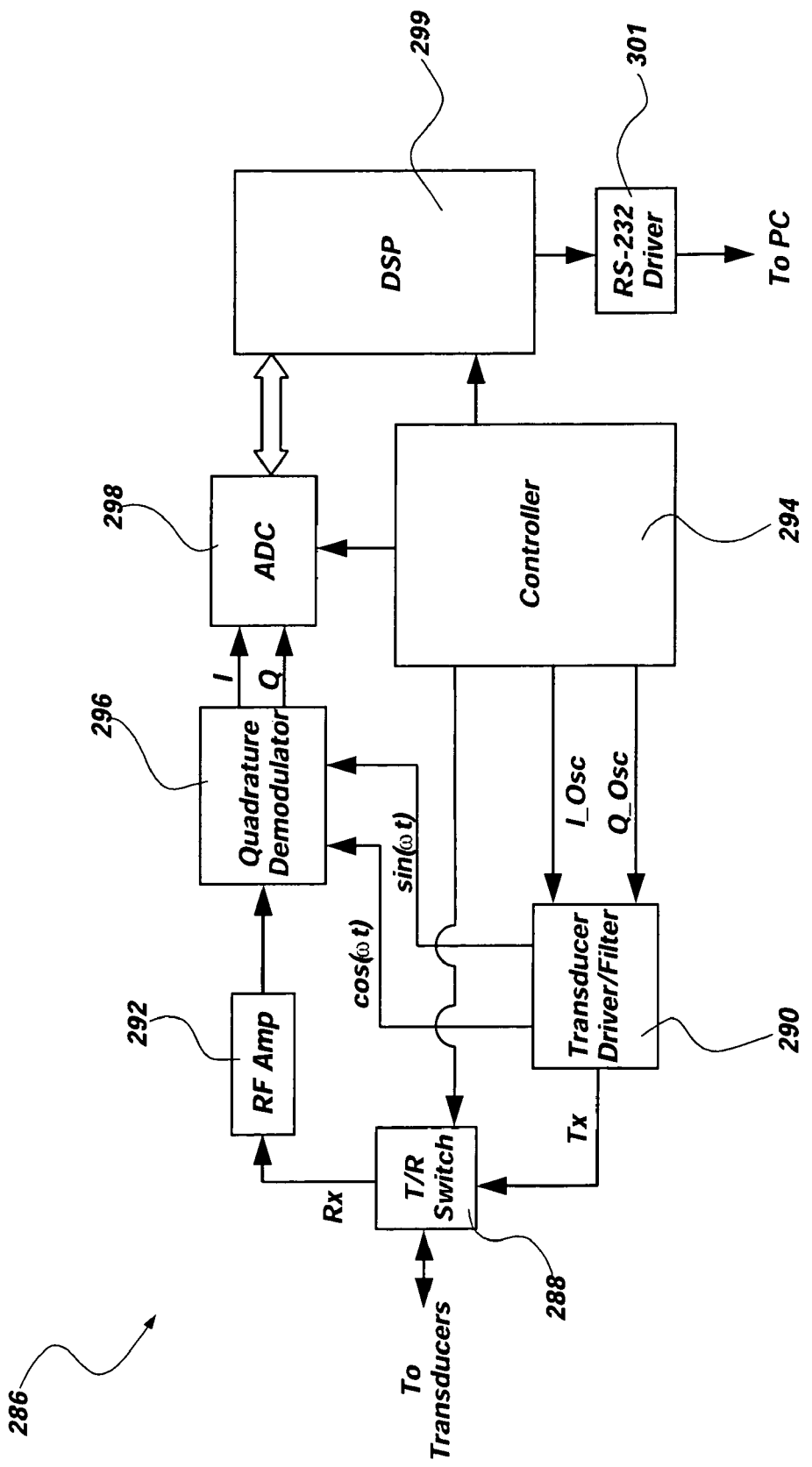
FIG. 7B is a block diagram of yet another embodiment of exemplary Doppler processing hardware for a second approach to "pulsed" Doppler suitable for use in the system of FIG. 5.

As shown in FIG. 7B, another embodiment of pulsed Doppler hardware 286, if used in the system of FIG. 5, includes transmit/receive switching hardware 288 coupled to two mutually separated groups of active imaging transducer elements of longitudinal transducer array 16 (see FIG. 7C), a transducer driver/filter 290 for transmitting pulsed signals and an RF amplifier 292 for receiving reflected pulsed signals. The transducer driver/filter 290 is coupled to and receives output from a controller 294 and to a quadrature demodulator 296, which receives output therefrom and which is also coupled to RF amplifier 292. Quadrature demodulator 296 is coupled and outputs to analog-to-digital converter ("ADC") 298, as does controller 294. ADC 298 outputs to digital signal processor ("DSP") 299. DSP 299 is coupled to and communicates with ADC 298. DSP 299 outputs to host computer 80 (see FIG. 5) through RS-232 driver 301. Data gathered by the two groups of active imaging elements acting as pulsed Doppler elements is manipulated as known in the art to provide blood flow direction and velocity data. The sign (positive or negative) of the output received from each channel, in association with relative magnitudes of the signals, is used to determine blood flow direction.

Figure 7C:
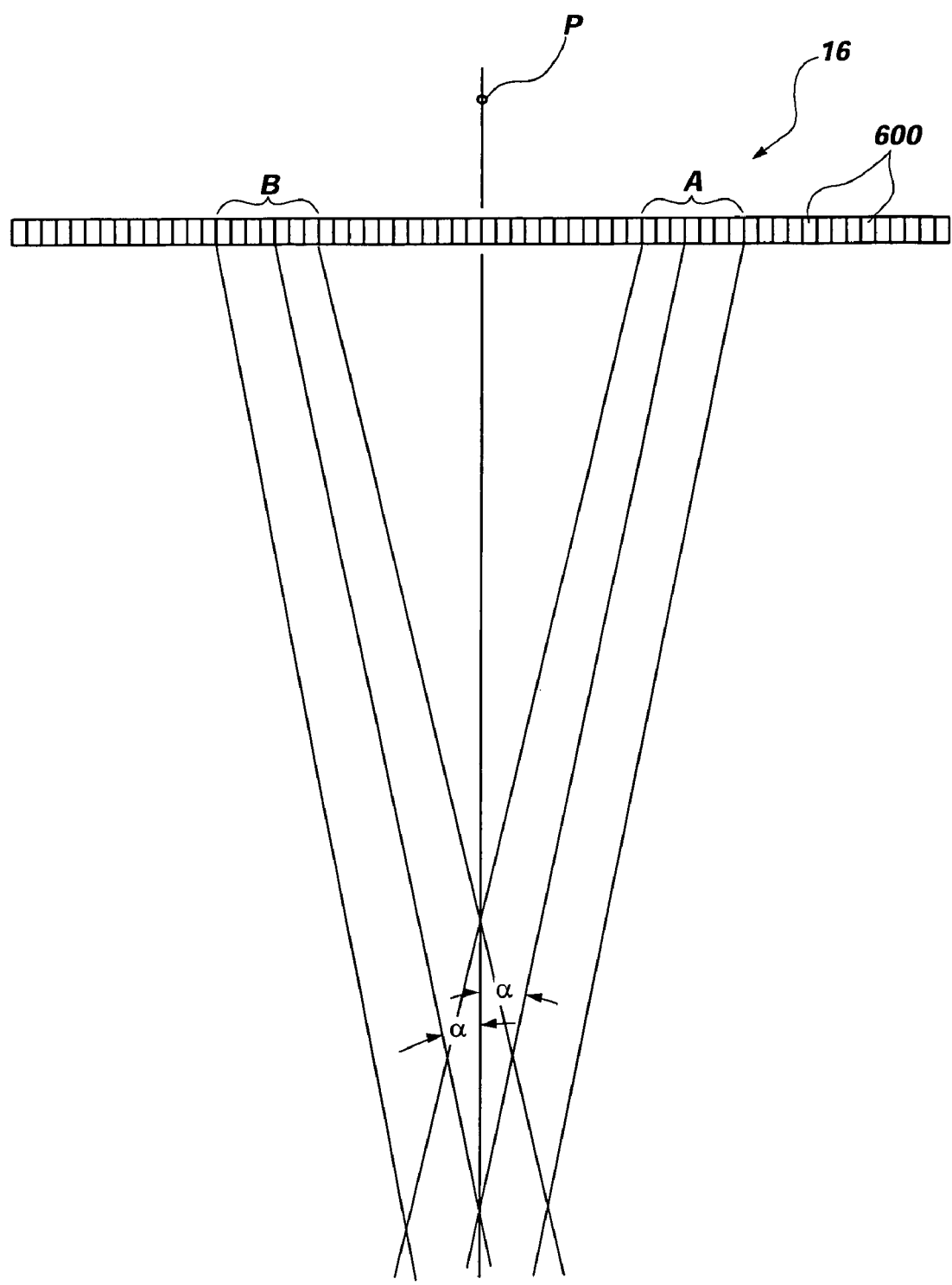
FIG. 7C is a schematic side elevation of a longitudinal imaging transducer array, wherein groups of active imaging transducer elements thereof are employed as Doppler elements in association with the components of FIG. 7B.

Referring to FIG. 7C, longitudinal transducer array 16 suitable for use with pulsed Doppler hardware 286 (FIG. 7B) comprises a plurality of piezoelectric active imaging elements 600, for example, sixty-four elements of 0.3 mm length each, forming an array of 19.2 mm length. FIG. 7C is greatly enlarged for clarity. Two groups A and B of elements 600, for example, seven elements 600 per group along a distance of 2.1 mm, are separated along the length of longitudinal transducer array 16 of, for example, 6.9 mm. Each group of elements 600 is employed as a pulsed Doppler element configured to emit and receive ultrasound signals at the same but opposing angle α, which may also be termed a "steering angle," to a perpendicular P to the plane of longitudinal transducer array 16 in association with the hardware described above with respect to FIG. 7B. Angle α may comprise a relatively small angle, for example 12.2°. It should be noted that this implementation of the present invention may be fabricated in a more compact form than those employing a separate Doppler element placed at the end of longitudinal transducer array 16, being as much as about 25% longitudinally shorter. Thus, for individuals having short necks, and especially children and infants, this implementation may provide significant advantages with respect to ease of placement and use.

Referring now to FIGS. 8A through 8D and 9A through 9D, another exemplary implementation of the sensor assembly 10 of the present invention is employed in combination with a magnetic reference location element 300 to form, in combination, an ultrasonic cannulation assembly of the present invention. In this variation, the elements of sensor assembly 10 are as previously described, with the exception of some aspects of cover 230. Elements and features previously described herein are identified by the same reference numerals in FIGS. 8A through 8D. Cover 230 is sized to conformally fit over housing 12 (not shown), which has been snapped into frame element 46 (see FIG. 4) associated with elongated, flexible, protective, transparent sheath 44 as previously described. Housing 12, which is placed inside elongated, flexible, protective, transparent sheath 44 over a mass of acoustic transmission gel is snapped into frame element 46, which is placed opposite the bottom of housing 12 on the outside of transparent sheath 44. Cover 230 is then placed over housing 12 from the outside of the transparent sheath 44 and snap-fit to frame element 46. Cover 230 includes wings 240 extending laterally from opposing sides thereof, each wing 240 carrying a magnet 242 disposed and secured in a downwardly facing cavity 244 thereof. It is currently preferred to use neodymium magnets, offered by Jobmaster Magnets of Randallstown, Md. Wings 240 are preferably formed as integral portions of cover 230, curve arcuately away from the sides of cover 230 (see FIG. 8B) and are sized in length and cross-section to permit upward and downward flexing (see arrows) to accommodate different neck circumferences. Gripping elements 246, to facilitate gripping by the hands of the clinician for manipulation of sensor assembly 10, are located on each side of cover 230. In this embodiment, arrows on the top of cover 230 (see FIG. 8A), which may be respectively colored red (for arterial flow) and blue (for venous flow), indicate direction and type of blood flow. Cover 230 also includes a vertical slit 250 (see FIG. 8B), which facilitates ejection of sensor assembly 10 therefrom after use and defines a notch comprising needle guide 40, which, when assembled with frame element 46, is coincident with a notch formed therein. Arrows on the end of cover 230 (see FIG. 8B) point toward needle guide 40.

As shown in FIGS. 9A through 9D, reference location element 300 comprises a film or tape 302 having an adhesive 304 thereon, adhesive 304 being covered by tape backing 306, which includes folded portion 306a to facilitate gripping thereof when it is desired to remove tape backing 306 for application of film or tape 302 to the neck or location on the body of a patient. Film or tape 302 comprises a sandwich or laminate of two individual films coated on their facing surfaces with an adhesive. Within the sandwich or laminate are disposed two metal discs or flexible polymer elements 310 of a magnetically sensitive or responsive material, such as zinc-plated steel shim stock; metal discs or flexible polymer elements 310 being symmetrically located on each side of centerline CL of magnetic reference location element 300. Recess or cutout 312 at the periphery of film or tape 302, which will be oriented toward the patient's head in use, facilitates needle insertion without having to penetrate film or tape 302.

Of course, magnets 242 may be placed on magnetic reference location element 300, while metal discs or flexible polymer elements 310 may be placed on cover 230, such arrangement being encompassed by the present invention. Furthermore, a magnetic tape comprising the aforementioned flexible polymer and in the form of an anisotropic conductive film, such as is used in refrigerator magnets, may be used in lieu of discrete magnets.

In use, the sensor assembly 10, secured within elongated, flexible, protective, transparent sheath 44 and having cover 230 placed thereover, is placed over magnetic reference location element 300, which has been adhered to the patient by pulling tape backing 306 off of adhesive 304 and applying film or tape 302 to the patient, adhesive-side down. An acoustic transmission gel has been placed over the outer surface of film or tape 302, and sensor assembly 10 is placed over reference location element 300 with each of magnets 242 at least partially superimposed over one metal disc or flexible polymer elements 310, which is sized in diameter slightly larger than magnets 242. Due to the magnetic attraction between magnets 242 and metal discs or flexible polymer elements 310, sensor assembly 10 is held firmly in place. However, the magnetic attraction is limited so that sensor assembly 10 may be moved laterally or vertically over reference location element 300 to position it precisely as previously described and for the purposes previously indicated.

It is also contemplated that other approaches for locating a sensor assembly on the patient are possible and encompassed by the present invention. For example, hook and loop fabrics, such as those offered by Velcro Corporation, may be employed. In one configuration, a collar for placement about the neck of a patient may be fabricated using, for example, a loop fabric on the exterior thereof and the sensor assembly may be provided with one or more patches of hook fabric for engaging the loop fabric of the collar to place, adjust and secure the sensor assembly to the collar. Alternatively, discs of loop fabric may be adhered to the skin of the patient and patches of hook fabric placed on the sensor assembly to place, adjust and secure the sensor assembly to the discs.

Further, while the present invention has been discussed for the sake of convenience in relation to cannulation of blood vessels, it is contemplated to have equal utility in placement of nerve blocks. For example, if it is desired to block the brachial plexus (a network of nerves formed by spinal nerves C5 to C8 and T1 with contributions from C4 and T2, which constitutes the entire nerve supply for the upper extremities, as well as a number of neck and shoulder muscles), the sensor assembly of the present invention may be used to visualize the adjacent artery and vein and to avoid the artery, vein and nerve bundle while placing the needle tip next to the nerve to initiate the block. Thus, the scope of the present invention encompasses the location of blood vessels for reference and locational purposes, regardless of whether the blood vessels or some other structure inside the body is of interest as a target location.

Figure 10A:
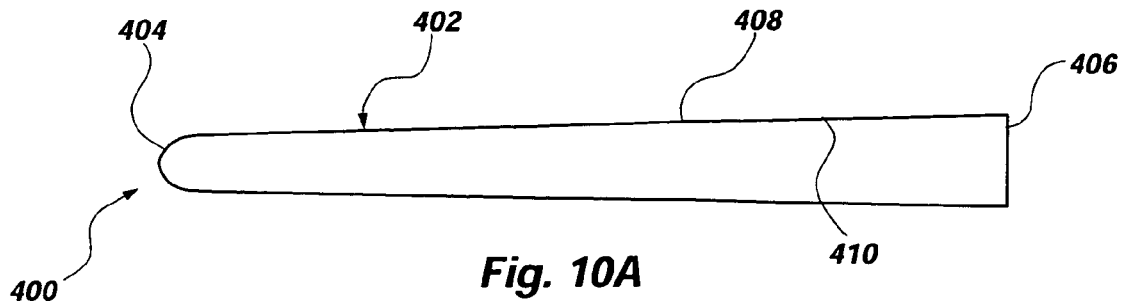
FIGS. 10A through 10D schematically depict a protective sheath and manipulation thereof for packaging and use, according to the present invention.
Figure 10B:
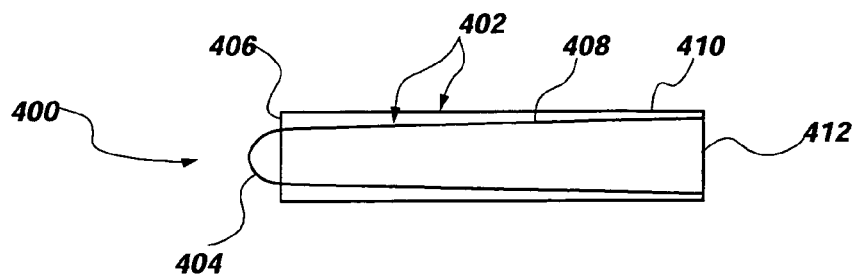
Figure 10C:
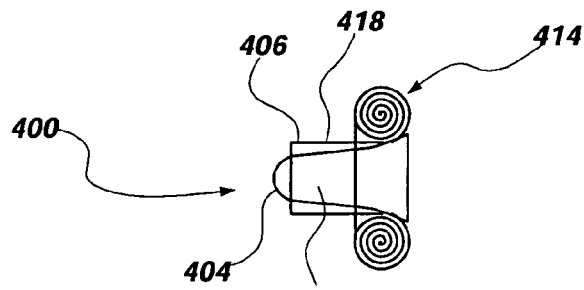
Figure 10D:
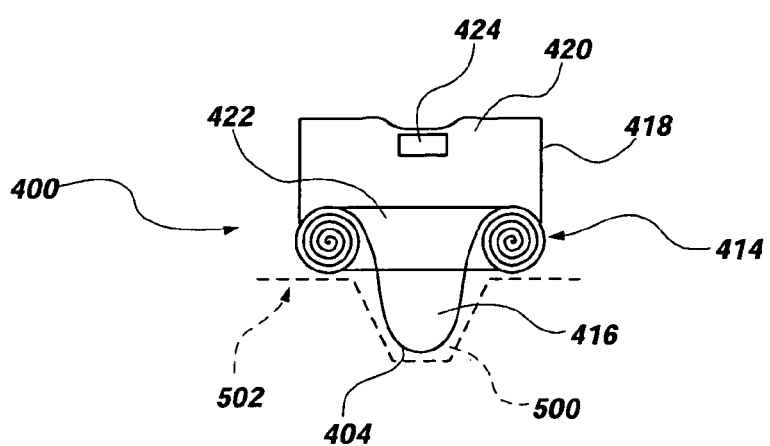

Referring now to FIGS. 10A through 10D of the drawings, an inventive embodiment 400 of elongated, flexible, transparent protective sheath 44 is depicted. As shown in FIG. 10A, inventive sheath 400 may comprise a low-density polyethylene polymer film defining a substantially tubular body 402 and having a closed end 404 and a first open end 406. If desired, tubular body 402 of sheath 400 may taper from a relatively smaller cross-section proximate closed end 404 to a relatively larger first open end 406, but this is not required. In preparation for ultimate use and for packaging, tubular body 402 is everted, or turned inside-out, by drawing first open end 406 back over the exterior surface 408 thereof until everted first open end 406 lies proximate the closed end 404 as shown in FIG. 10B, so that a portion of the former interior surface 410 of sheath 400 now lies on the exterior thereof and a second open end 412 is created at the opposite end of everted sheath 400 from closed end 404 and first open end 406. The polymer film at second open end 412 is then rolled outwardly over the doubled polymer film to form a toroidal shape 414 of rolled, doubled polymer film until a location proximate the closed end 404 is reached, leaving a pouch 416 surrounded by a skirt 418 of polymer film comprising everted first open end 406, as shown in FIG. 10C. Skirt 418 is then folded back over the toroidal shape 414 of rolled, doubled polymer film, the resulting structure being shown in FIG. 10D. As also shown in FIG. 10D, the resulting structure may be placed in a cavity 500 in a tray 502 with the upper mouth 420 of the folded-back skirt 418 facing upwardly, as is the lower mouth 422 of toroidal shape 414 of rolled, doubled polymer film opening into pouch 416. The tray 502, with sheath 400, frame element 46, cover 230, reference location element 300, sterile acoustic transmission gel, cotton gauze pads, cotton swabs, user guide and cautionary statement, is then packaged and sterilized, as known in the art. At the surgical theatre or other location of use, a sensor assembly 10 may be easily inserted into sterile pouch 416 by an individual after disposition of acoustic transmission gel therein as previously discussed, after which another individual may grasp the lower mouth 422 of folded-back skirt 418 proximal to upper mouth 420 and pull sheath 400 back to extend it along and over multi-conductor cable 20, the sterility of the exterior of sheath 400 thus being maintained free from potential contamination by the nonsterile sensor assembly 10 and multi-conductor cable 20 on the interior thereof. The extension of the sheath 400 may be facilitated by affixing two tabs 424 of, for example, paper, cardboard or a polymer proximate the edge of folded-back skirt 418, the tabs 424 being affixed at opposite sides of the edge of folded-back skirt 418. The tabs 424, which may be brightly colored to aid visibility, aid the individual who grasps and extends the sheath 400 by providing an easily seen visual landmark or reference point on an otherwise transparent and featureless edge of folded-back skirt 418. It is envisioned that the individual who extends sheath 400 may place the thumb and forefinger of each hand, respectively, on a pull tab 424, grasping the pull tabs 424 adjacent the edge of folded-back skirt 418 and gently pulling in order to extend sheath 400. Sterile frame element 46 and cover 230 may then be assembled with housing 12 of sensor assembly 10 and a procedure performed, as previously described. Of course, the protective sheath 400 is not limited to use with the inventive sensor assembly 10 of the present invention, but may be employed with any sensor introducible thereinto.

Referring now to FIGS. 11A through 11C and 12, a variation of the embodiment of FIGS. 8A through 8C is depicted. In this variation, wings 240 carrying magnets 242 at distal ends thereof extend laterally from opposing sides of a frame element 546, which comprises sidewalls 548 defining a central opening 550. As depicted, central opening 550 may be substantially rectangular with slightly convex sides; however, this is not a requirement of the invention. Tabs 552 having outwardly flared ends 554 extend upwardly from opposing side walls sidewalls 548 on opposite sides of wings 240. Tabs 552 include downwardly facing shoulders 556 facing central opening 550. One or both tabs 552 may have a needle guide comprising an arrow A printed on an exterior surface thereof, as depicted in FIG. 11B. Sidewalls 548 and tabs 552 are configured, in combination, to receive a sensor assembly housing 512 containing a sensor assembly 10 as previously described as shown in broken lines in FIGS. 11B and 11C after the sensor assembly 10 contained within housing 512 is inserted within an elongated, flexible, protective transparent sheath 44 (not shown in FIGS. 11A through 11C) having an acoustic transmission gel disposed within the closed end thereof, as previously described. As noted previously with respect to housing 12 and frame element 46, housing 512 is snapped into frame element 546. When received within frame element 546, shoulders 556 of frame element 546 abut lips 514 on the exterior of housing 512 holding housing 512 against and partially extending within central opening 550 of a frame element 546 defined by sidewalls 548, the acoustic transmission gel thus being located between the lower face of sensor assembly 10 and a portion of transparent sheath 44. When the resulting assembly is placed on a patient's skin, the lower face of sensor assembly 10 (which is exposed through central opening 550) may contact the skin through the acoustic gel and the thin film material of transparent sheath 44. In use, the resulting assembly may be placed over a reference location element 300 as previously described with respect to FIGS. 9A through 9B, and used in cooperation therewith, also as previously described. As depicted in FIG. 12, in this variation, housing 512 bears transverse grid markings 32 and longitudinal grid markings 34 on an upper surface thereof, thus eliminating the use of a protective cover. The grid markings are easily visible to the clinician through the transparent material of elongated, flexible, protective transparent sheath 44 (not shown). Also as depicted in FIG. 12, cable 20 extends laterally from a side of housing 512 so as to extend between, and clear, tabs 552 when housing 512 is snapped into frame element 546.

Although the present invention has been described with reference to particular embodiments, the invention is not limited to these described embodiments. Rather, the invention is limited only by the appended claims, which include within their scope all equivalent devices or methods that operate according to the principles of the invention as described.

What is claimed is:

1. An apparatus for sensing a presence and orientation of one or more vessels within a portion of a patient's body for insertion of a needle into a target vessel, the apparatus comprising:
a sensor assembly including:
a housing having disposed therewithin a plurality of transducer arrays consisting essentially of:
a first linear, ultrasonic transducer array comprising a plurality of elements aimed substantially perpendicular to a linear direction of the first linear, ultrasonic transducer array; and
a second linear, ultrasonic transducer array comprising a plurality of elements, positioned perpendicular to the first linear, ultrasonic transducer array to form a T shape therewith and oriented in a plane substantially parallel to a plane of the first linear, ultrasonic transducer array, aimed substantially perpendicular to a linear direction of the second linear, ultrasonic transducer array;
the plurality of elements of the first linear, ultrasonic transducer array and the plurality of elements of the second linear, ultrasonic transducer array being aimed in a common direction substantially perpendicular to the plane of the first linear, ultrasonic transducer array and the plane of the second linear, ultrasonic transducer array;
wherein the housing includes an exterior surface bearing a grid system comprising a first plurality of linearly spaced, longitudinal grid markings parallel to a body of the T superimposed over and aligned with the first linear, ultrasonic transducer array and a second plurality of linearly spaced, transverse grid markings parallel to a head of the T superimposed over and aligned with the second linear, ultrasonic transducer array, the first and second pluralities of linearly spaced grid markings each comprising value indicia representative of positions along their respectively associated first and second linear, ultrasonic transducer arrays indicative of positions of the plurality of elements of the first and second linear, ultrasonic transducer arrays on a surface of the patient's body with the housing located on the patient's body and the elements of the first and second linear, ultrasonic transducer arrays aimed into the patient's body;
a needle guide proximate one end of the housing adjacent the head of the T; and
a monitoring system, including:
a beamformer operably coupled to the first and second linear, ultrasonic transducer arrays;
a converter operably coupled to the beamformer for converting signals therefrom to images respectively depicting a transverse sectional view and a longitudinal sectional view of a portion of the patient's body interior of the housing, the images comprising one or more vessels in the portion of the patient's body and a location and orientation of a needle associated with the needle guide and inserted in the portion of the patient's body adjacent the one or more vessels;
a computer operably coupled to the converter;
a display device operably coupled to the computer and configured to simultaneously display the images respectively depicting transverse sectional and longitudinal sectional views of the portion of the patient's body and the location and orientation of the needle in relation to the one or more vessels and the displayed longitudinal grid markings and transverse grid markings, each of the displayed longitudinal grid marking and transverse grid markings comprising value indicia correlated respectively to the value indicia of the longitudinal grid markings and transverse grid markings of the grid system on the exterior surface of the housing to enable orientation and positioning of the housing and of the needle guide with respect to a target vessel by using the displayed images in conjunction with the displayed grid markings.

2. The apparatus of claim 1, further including a frame element engaged with the housing, with a face of the sensor assembly through which the elements of the first and second linear, ultrasonic arrays are aimed disposed within an opening through the frame element and on a side of the housing opposite the grid system for placement proximate the skin of a patient.

3. The apparatus of claim 2, further including a pair of wings extending laterally from locations adjacent opposing sides of the frame element beyond the housing, each wing of the pair carrying a permanent magnet at an end thereof remote from the housing.

4. The apparatus of claim 3, wherein the needle guide is proximate one end of the frame element on a sidewall thereof located between the wings.

5. The apparatus of claim 4, wherein the needle guide comprises a marking on the sidewall of the frame element.

6. The apparatus of claim 2, wherein the frame element includes tab elements extending upwardly substantially perpendicular to a plane of the frame element from opposing sidewalls thereof, and the housing is engaged with the sidewalls of the frame element and the tab elements.

7. The apparatus of claim 6, wherein each tab element includes a downwardly facing shoulder thereon engaged with a surface of the housing.

8. The apparatus of claim 2, further comprising an elongated, protective, flexible sheath open at one end thereof, the frame element circumferentially clamping a portion of another, closed end of the sheath against the face of the sensor assembly.

9. The apparatus of claim 8, further including an acoustic transmission gel disposed between the portion of the closed end of the sheath and the face of the sensor assembly.

10. The apparatus of claim 3, further including a reference location element for securing to the skin of a patient over a target vessel, the reference location element comprising a film carrying two elements of magnetically sensitive material spaced about a same distance as a distance between the permanent magnets carried by the wings extending laterally from locations adjacent opposing sides of the frame element for cooperative magnetic engagement between a permanent magnet carried by a frame element wing and an element of magnetically sensitive material carried by the film, each element of magnetically sensitive material having at least one greater lateral dimension than a lateral dimension of one of the permanent magnets, the film including an adhesive thereon for affixation to the patient's skin.

11. The apparatus of claim 1, wherein:
the converter comprises a dual B-mode digital scan converter.

* * * * *